United States Patent
Weber et al.

(10) Patent No.: US 10,750,983 B2
(45) Date of Patent: Aug. 25, 2020

(54) PHYSIOLOGICAL MEASUREMENT SYSTEM WITH AUTOMATIC WAVELENGTH ADJUSTMENT

(71) Applicant: Cercacor Laboratories, Inc., Irvine, CA (US)

(72) Inventors: Walter M. Weber, Laguna Hills, CA (US); Ammar Al-Ali, San Juan Capistrano, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 464 days.

(21) Appl. No.: 15/812,930

(22) Filed: Nov. 14, 2017

(65) Prior Publication Data
US 2018/0132769 A1 May 17, 2018

Related U.S. Application Data

(63) Continuation of application No. 12/949,271, filed on Nov. 18, 2010, now Pat. No. 9,839,381.

(60) Provisional application No. 61/330,253, filed on Apr. 30, 2010, provisional application No. 61/264,182, filed on Nov. 24, 2009.

(51) Int. Cl.
*A61B 5/1455* (2006.01)
*A61B 5/00* (2006.01)
*A61B 5/0205* (2006.01)

(52) U.S. Cl.
CPC ........ *A61B 5/14551* (2013.01); *A61B 5/0059* (2013.01); *A61B 5/0205* (2013.01); *A61B 5/7203* (2013.01); *A61B 5/7221* (2013.01); *A61B 5/0075* (2013.01)

(58) Field of Classification Search
CPC . A61B 5/1455; A61B 5/14551; A61B 5/0059; A61B 5/7221; A61B 5/0205; A61B 5/7203; A61B 5/0075; A61B 5/14532
See application file for complete search history.

(56) References Cited

U.S. PATENT DOCUMENTS

| 3,316,395 A | 4/1967 | Lavin |
| 3,316,396 A | 4/1967 | Lavin |
| 3,910,701 A | 10/1975 | Henderson et al. |

(Continued)

FOREIGN PATENT DOCUMENTS

| EP | 0 231 379 | 8/1987 |
| EP | 41 92 23 | 3/1991 |

(Continued)

OTHER PUBLICATIONS

US 8,845,543 B2, 09/2014, Diab et al. (withdrawn)

(Continued)

*Primary Examiner* — Eric F Winakur
*Assistant Examiner* — Chu Chuan Liu
(74) *Attorney, Agent, or Firm* — Knobbe Martens Olson & Bear LLP

(57) ABSTRACT

Disclosed herein is a physiological measurement system that can automatically adjust the number of wavelengths used based on the quality of a sensor signal that is reflective of an optical radiation detected at a sensor after tissue attenuation. The signal quality is examined to determine if it is sufficient to support the use of a full set of wavelengths. If it is determined to be insufficient to support the full set, a reduced number of wavelengths is used.

20 Claims, 17 Drawing Sheets

(56) References Cited

U.S. PATENT DOCUMENTS

| | | |
|---|---|---|
| 3,998,550 A | 12/1976 | Konishi et al. |
| 4,014,321 A | 3/1977 | March |
| 4,051,522 A | 9/1977 | Healy et al. |
| 4,134,678 A | 1/1979 | Brown et al. |
| 4,157,708 A | 6/1979 | Imura |
| 4,163,290 A | 7/1979 | Sutherlin et al. |
| 4,167,331 A | 9/1979 | Nielsen |
| 4,266,554 A | 5/1981 | Hamaguri |
| 4,267,844 A | 5/1981 | Yamanishi |
| 4,305,059 A | 12/1981 | Benton |
| 4,446,871 A | 5/1984 | Imura |
| 4,491,725 A | 1/1985 | Pritchard |
| 4,531,527 A | 7/1985 | Reinhold, Jr. et al. |
| 4,586,513 A | 5/1986 | Hamaguri |
| 4,621,643 A | 11/1986 | New et al. |
| 4,653,498 A | 3/1987 | New, Jr. et al. |
| 4,655,225 A | 4/1987 | Dahne et al. |
| 4,685,464 A | 8/1987 | Goldberger et al. |
| 4,694,833 A | 9/1987 | Hamaguri |
| 4,695,955 A | 9/1987 | Faisandier |
| 4,700,708 A | 10/1987 | New et al. |
| 4,714,341 A | 12/1987 | Hamaguri et al. |
| 4,770,179 A | 9/1988 | New et al. |
| 4,773,422 A | 9/1988 | Isaacson et al. |
| 4,781,195 A | 11/1988 | Martin |
| 4,800,885 A | 1/1989 | Johnson |
| 4,805,623 A | 2/1989 | Jobsis |
| 4,832,484 A | 5/1989 | Aoyagi et al. |
| 4,846,183 A | 7/1989 | Martin |
| 4,854,328 A | 8/1989 | Pollack |
| 4,863,265 A | 9/1989 | Flower et al. |
| 4,867,571 A | 9/1989 | Frick et al. |
| 4,869,254 A | 9/1989 | Stone et al. |
| 4,907,876 A | 3/1990 | Suzuki et al. |
| 4,911,167 A | 3/1990 | Corenman et al. |
| 4,934,372 A | 6/1990 | Corenman et al. |
| 4,938,218 A | 7/1990 | Goodman et al. |
| 4,942,877 A | 7/1990 | Sakai et al. |
| 4,955,379 A | 9/1990 | Hall |
| 4,960,126 A | 10/1990 | Conlon et al. |
| 4,960,128 A | 10/1990 | Gordon et al. |
| 4,964,010 A | 10/1990 | Miyasaka et al. |
| 4,964,408 A | 10/1990 | Hink et al. |
| 4,967,571 A | 11/1990 | Sporri |
| 4,975,581 A | 12/1990 | Robinson et al. |
| 4,986,665 A | 1/1991 | Yamanishi et al. |
| 4,997,769 A | 3/1991 | Lundsgaard |
| 5,025,791 A | 6/1991 | Niwa |
| RE33,643 E | 7/1991 | Isaacson et al. |
| 5,028,787 A | 7/1991 | Rosenthal et al. |
| 5,033,472 A | 7/1991 | Sato et al. |
| 5,041,187 A | 8/1991 | Hink et al. |
| 5,054,495 A | 10/1991 | Uemura et al. |
| 5,058,588 A | 10/1991 | Kaestle et al. |
| 5,069,213 A | 12/1991 | Polczynski |
| 5,077,476 A | 12/1991 | Rosenthal |
| 5,078,136 A | 1/1992 | Stone et al. |
| 5,101,825 A | 4/1992 | Gravensetin et al. |
| 5,137,023 A | 8/1992 | Mendelson et al. |
| 5,163,438 A | 11/1992 | Gordon et al. |
| 5,188,108 A | 2/1993 | Secker |
| 5,189,609 A | 2/1993 | Tivig et al. |
| 5,190,040 A | 3/1993 | Aoyagi |
| 5,203,329 A | 4/1993 | Takatani et al. |
| 5,209,230 A | 5/1993 | Swedlow et al. |
| 5,226,053 A | 7/1993 | Cho et al. |
| 5,246,002 A | 9/1993 | Prosser |
| 5,247,931 A | 9/1993 | Norwood |
| 5,259,381 A | 11/1993 | Chung |
| 5,267,562 A | 12/1993 | Ukawa et al. |
| 5,267,563 A | 12/1993 | Swedlow et al. |
| 5,278,627 A | 1/1994 | Aoyagi |
| 5,297,548 A | 3/1994 | Pologe |
| 5,313,940 A | 5/1994 | Fuse et al. |
| 5,319,355 A | 6/1994 | Russek |
| 5,331,549 A | 7/1994 | Crawford, Jr. |
| 5,335,659 A | 8/1994 | Pologe et al. |
| 5,337,744 A | 8/1994 | Branigan |
| 5,337,745 A | 8/1994 | Benaron |
| 5,341,805 A | 8/1994 | Stavridi et al. |
| 5,348,004 A | 9/1994 | Hollub |
| 5,351,685 A | 10/1994 | Potratz |
| 5,355,880 A | 10/1994 | Thomas et al. |
| 5,355,882 A | 10/1994 | Ukawa et al. |
| 5,361,758 A | 11/1994 | Hall et al. |
| 5,368,224 A | 11/1994 | Richardson et al. |
| D353,195 S | 12/1994 | Savage et al. |
| D353,196 S | 12/1994 | Savage et al. |
| 5,372,136 A | 12/1994 | Steuer et al. |
| 5,377,676 A | 1/1995 | Vari et al. |
| 5,385,143 A | 1/1995 | Aoyagi |
| 5,387,122 A | 2/1995 | Goldberger et al. |
| 5,392,777 A | 2/1995 | Swedlow et al. |
| 5,413,101 A | 5/1995 | Sugiura |
| D359,546 S | 6/1995 | Savage et al. |
| 5,421,329 A | 6/1995 | Casciani et al. |
| 5,424,545 A | 6/1995 | Block et al. |
| 5,427,093 A | 6/1995 | Ogawa et al. |
| 5,429,128 A | 7/1995 | Cadell et al. |
| 5,431,170 A | 7/1995 | Mathews |
| 5,435,309 A | 7/1995 | Thomas et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| RE35,122 E | 12/1995 | Corenman et al. |
| 5,479,934 A | 1/1996 | Imran |
| 5,482,036 A | 1/1996 | Diab et al. |
| 5,490,505 A | 2/1996 | Diab et al. |
| 5,490,523 A | 2/1996 | Isaacson et al. |
| 5,494,032 A | 2/1996 | Robinson et al. |
| 5,494,043 A | 2/1996 | O'Sullivan et al. |
| 5,503,148 A | 4/1996 | Pologe et al. |
| 5,520,177 A | 5/1996 | Ogawa |
| 5,533,507 A | 7/1996 | Potratz |
| 5,533,511 A | 7/1996 | Kaspari et al. |
| 5,534,851 A | 7/1996 | Russek |
| 5,551,423 A | 9/1996 | Sugiura |
| 5,553,615 A | 9/1996 | Carim et al. |
| 5,555,882 A | 9/1996 | Richardson et al. |
| 5,561,275 A | 10/1996 | Savage et al. |
| 5,562,002 A | 10/1996 | Lalin |
| 5,575,284 A | 11/1996 | Athan et al. |
| 5,577,500 A | 11/1996 | Potratz |
| 5,584,299 A | 12/1996 | Sakai et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,596,992 A | 1/1997 | Haaland et al. |
| 5,602,924 A | 2/1997 | Durand et al. |
| 5,603,623 A | 2/1997 | Nishikawa et al. |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,106 A | 9/1997 | Swedlow et al. |
| 5,676,139 A | 10/1997 | Goldberger et al. |
| 5,676,141 A | 10/1997 | Hollub |
| 5,678,544 A | 10/1997 | Delonzor et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,690,104 A | 11/1997 | Kanemoto et al. |
| 5,692,503 A | 12/1997 | Kuenstner |
| 5,697,371 A | 12/1997 | Aoyagi |
| 5,800,348 A | 1/1998 | Kaestle et al. |
| 5,713,355 A | 2/1998 | Richardson et al. |

(56) References Cited

U.S. PATENT DOCUMENTS

| | | |
|---|---|---|
| 5,719,589 A | 2/1998 | Norman et al. |
| 5,720,284 A | 2/1998 | Aoyagi et al. |
| 5,730,125 A | 3/1998 | Prutchi et al. |
| D393,830 S | 4/1998 | Tobler et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,587 A | 6/1998 | Gratton et al. |
| 5,779,630 A | 7/1998 | Fein et al. |
| 5,782,237 A | 7/1998 | Casciani et al. |
| 5,782,756 A | 7/1998 | Mannheimer |
| 5,782,757 A | 7/1998 | Diab et al. |
| 5,785,659 A | 7/1998 | Caro et al. |
| 5,790,729 A | 8/1998 | Pologe et al. |
| 5,791,347 A | 8/1998 | Flaherty et al. |
| 5,792,052 A | 8/1998 | Isaacson et al. |
| 5,793,485 A | 8/1998 | Gourley |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,810,723 A | 9/1998 | Aldrich |
| 5,810,724 A | 9/1998 | Gronvall |
| 5,810,734 A | 9/1998 | Caro et al. |
| 5,817,010 A | 10/1998 | Hibl |
| 5,818,985 A | 10/1998 | Merchant et al. |
| 5,823,950 A | 10/1998 | Diab et al. |
| 5,823,952 A | 10/1998 | Levinson et al. |
| 5,827,182 A | 10/1998 | Raley et al. |
| 5,830,131 A | 11/1998 | Caro et al. |
| 5,830,137 A | 11/1998 | Sharf |
| 5,833,602 A | 11/1998 | Osemwota |
| 5,833,618 A | 11/1998 | Caro et al. |
| 5,839,439 A | 11/1998 | Nierlich et al. |
| RE36,000 E | 12/1998 | Swedlow et al. |
| 5,842,979 A | 12/1998 | Jarman |
| 5,851,178 A | 12/1998 | Aronow |
| 5,851,179 A | 12/1998 | Ritson et al. |
| 5,853,364 A | 12/1998 | Baker, Jr. et al. |
| 5,857,462 A | 1/1999 | Thomas et al. |
| 5,860,919 A | 1/1999 | Kiani-Azarbayjany et al. |
| 5,865,736 A | 2/1999 | Baker, Jr. et al. |
| 5,876,348 A | 3/1999 | Sugo |
| 5,885,213 A | 3/1999 | Richardson et al. |
| 5,890,929 A | 4/1999 | Mills et al. |
| 5,891,022 A | 4/1999 | Pologe |
| 5,891,024 A | 4/1999 | Jarman et al. |
| 5,904,654 A | 5/1999 | Wohltmann et al. |
| 5,910,108 A | 6/1999 | Solenberger |
| 5,916,154 A | 6/1999 | Hobbs et al. |
| 5,919,133 A | 7/1999 | Taylor |
| 5,919,134 A | 7/1999 | Diab |
| 5,921,921 A | 7/1999 | Potratz et al. |
| 5,924,979 A | 7/1999 | Swedlow |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling |
| 5,978,691 A | 11/1999 | Mills |
| 5,983,122 A | 11/1999 | Jarman et al. |
| 5,995,855 A | 11/1999 | Kiani et al. |
| 5,995,856 A | 11/1999 | Mannheimer et al. |
| 5,995,859 A | 11/1999 | Takahashi |
| 5,997,343 A | 12/1999 | Mills et al. |
| 5,999,841 A | 12/1999 | Aoyagi et al. |
| 6,002,952 A | 12/1999 | Diab et al. |
| 6,006,119 A | 12/1999 | Soller et al. |
| 6,011,986 A | 1/2000 | Diab et al. |
| 6,014,576 A | 1/2000 | Raley |
| 6,018,673 A | 1/2000 | Chin et al. |
| 6,018,674 A | 1/2000 | Aronow |
| 6,023,541 A | 2/2000 | Merchant et al. |
| 6,027,452 A | 2/2000 | Flaherty et al. |
| 6,036,642 A | 3/2000 | Diab et al. |
| 6,045,509 A | 4/2000 | Caro et al. |
| 6,064,898 A | 5/2000 | Aldrich |
| 6,067,462 A | 5/2000 | Diab et al. |
| 6,068,594 A | 5/2000 | Schloemer et al. |
| 6,073,037 A | 6/2000 | Alam et al. |
| 6,081,735 A | 6/2000 | Diab et al. |
| 6,083,172 A | 7/2000 | Baker, Jr. et al. |
| 6,088,607 A | 7/2000 | Diab et al. |
| 6,094,592 A | 7/2000 | Yorkey et al. |
| 6,104,938 A | 8/2000 | Huiku |
| 6,110,522 A | 8/2000 | Lepper, Jr. et al. |
| 6,112,107 A | 8/2000 | Hannula |
| 6,122,042 A | 9/2000 | Wunderman et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,149,588 A | 11/2000 | Noda et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,041 A | 12/2000 | Thomas et al. |
| 6,157,850 A | 12/2000 | Diab et al. |
| 6,165,005 A | 12/2000 | Mills et al. |
| 6,174,283 B1 | 1/2001 | Nevo et al. |
| 6,184,521 B1 | 2/2001 | Coffin et al. |
| 6,192,261 B1 | 2/2001 | Gratton et al. |
| 6,206,830 B1 | 3/2001 | Diab et al. |
| 6,226,539 B1 | 5/2001 | Potratz |
| 6,229,856 B1 | 5/2001 | Diab et al. |
| 6,230,035 B1 | 5/2001 | Aoyagi et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,256,523 B1 | 7/2001 | Diab et al. |
| 6,262,698 B1 | 7/2001 | Blum |
| 6,263,222 B1 | 7/2001 | Diab et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,301,493 B1 | 10/2001 | Marro et al. |
| 6,304,675 B1 | 10/2001 | Osbourn et al. |
| 6,304,767 B1 | 10/2001 | Soller et al. |
| 6,317,627 B1 | 11/2001 | Ennen et al. |
| 6,321,100 B1 | 11/2001 | Parker |
| 6,325,761 B1 | 12/2001 | Jay |
| 6,330,468 B1 | 12/2001 | Scharf |
| 6,334,065 B1 | 12/2001 | Al-Ali et al. |
| 6,341,257 B1 | 1/2002 | Haaland |
| 6,343,224 B1 | 1/2002 | Parker |
| 6,349,228 B1 | 2/2002 | Kiani et al. |
| 6,351,658 B1 | 2/2002 | Middleman et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,363,269 B1 | 3/2002 | Hanna et al. |
| 6,368,283 B1 | 4/2002 | Xu et al. |
| 6,371,921 B1 | 4/2002 | Caro et al. |
| 6,374,129 B1 | 4/2002 | Chin et al. |
| 6,377,828 B1 | 4/2002 | Chaiken et al. |
| 6,377,829 B1 | 4/2002 | Al-Ali |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,402,690 B1 | 6/2002 | Rhee et al. |
| 6,408,198 B1 | 6/2002 | Hanna et al. |

(56) References Cited

U.S. PATENT DOCUMENTS

| | | |
|---|---|---|
| 6,411,833 B1 | 6/2002 | Baker, Jr. et al. |
| 6,415,166 B1 | 7/2002 | Van Hoy et al. |
| 6,415,233 B1 | 7/2002 | Haaland |
| 6,415,236 B2 | 7/2002 | Kobayashi et al. |
| 6,421,549 B1 | 7/2002 | Jacques |
| 6,430,437 B1 | 8/2002 | Marro |
| 6,430,525 B1 | 8/2002 | Weber et al. |
| 6,434,408 B1 | 8/2002 | Heckel |
| 6,441,388 B1 | 8/2002 | Thomas et al. |
| 6,453,184 B1 | 9/2002 | Hyogo et al. |
| 6,455,340 B1 | 9/2002 | Chua et al. |
| 6,463,310 B1 | 10/2002 | Swedlow et al. |
| 6,463,311 B1 | 10/2002 | Diab |
| 6,466,824 B1 | 10/2002 | Struble |
| 6,470,199 B1 | 10/2002 | Kopotic et al. |
| 6,480,729 B2 | 11/2002 | Stone |
| 6,490,466 B1 | 12/2002 | Fein et al. |
| 6,497,659 B1 | 12/2002 | Rafert |
| 6,501,974 B2 | 12/2002 | Huiku |
| 6,501,975 B2 | 12/2002 | Diab et al. |
| 6,504,943 B1 | 1/2003 | Sweatt et al. |
| 6,505,059 B1 | 1/2003 | Kollias et al. |
| 6,505,060 B1 | 1/2003 | Norris |
| 6,505,061 B2 | 1/2003 | Larson |
| 6,505,133 B1 | 1/2003 | Hanna |
| 6,510,329 B2 | 1/2003 | Heckel |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,522,398 B2 | 2/2003 | Cadell et al. |
| 6,525,386 B1 | 2/2003 | Mills et al. |
| 6,526,300 B1 | 2/2003 | Kiani et al. |
| 6,526,301 B2 | 2/2003 | Larsen et al. |
| 6,528,809 B1 | 3/2003 | Thomas et al. |
| 6,537,225 B1 | 3/2003 | Mills |
| 6,541,756 B2 | 4/2003 | Schulz et al. |
| 6,542,763 B1 | 4/2003 | Yamashita et al. |
| 6,542,764 B1 | 4/2003 | Al-Ali et al. |
| 6,545,652 B1 | 4/2003 | Tsuji |
| 6,546,267 B1 | 4/2003 | Sugiura |
| 6,553,241 B2 | 4/2003 | Mannheimer et al. |
| 6,564,077 B2 | 5/2003 | Mortara |
| 6,571,113 B1 | 5/2003 | Fein et al. |
| 6,580,086 B1 | 6/2003 | Schulz et al. |
| 6,582,964 B1 | 6/2003 | Samsoondar et al. |
| 6,584,336 B1 | 6/2003 | Ali et al. |
| 6,584,413 B1 | 6/2003 | Keenan et al. |
| 6,591,123 B2 | 7/2003 | Fein et al. |
| 6,594,511 B2 | 7/2003 | Stone et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,609,016 B1 | 8/2003 | Lynn |
| 6,611,698 B1 | 8/2003 | Yamashita et al. |
| 6,614,521 B2 | 9/2003 | Samsoondar et al. |
| 6,615,064 B1 | 9/2003 | Aldrich |
| 6,615,151 B1 | 9/2003 | Scecina et al. |
| 6,618,602 B2 | 9/2003 | Levin |
| 6,622,095 B2 | 9/2003 | Kobayashi et al. |
| 6,628,975 B1 | 9/2003 | Fein et al. |
| 6,631,281 B1 | 10/2003 | Kastle |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,623 B1 | 11/2003 | Kastle |
| 6,654,624 B2 | 11/2003 | Diab et al. |
| 6,657,717 B2 | 12/2003 | Cadell et al. |
| 6,658,276 B2 | 12/2003 | Diab et al. |
| 6,658,277 B2 | 12/2003 | Wasserman |
| 6,661,161 B1 | 12/2003 | Lanzo et al. |
| 6,662,033 B2 | 12/2003 | Casciani et al. |
| 6,665,551 B1 | 12/2003 | Suzuki |
| 6,668,183 B2 | 12/2003 | Hicks et al. |
| 6,671,526 B1 | 12/2003 | Aoyagi et al. |
| 6,671,531 B2 | 12/2003 | Al-Ali et al. |
| 6,675,031 B1 | 1/2004 | Porges et al. |
| 6,675,106 B1 | 1/2004 | Keenan et al. |
| 6,678,543 B2 | 1/2004 | Diab et al. |
| 6,681,126 B2 | 1/2004 | Solenberger |
| 6,684,090 B2 | 1/2004 | Ali et al. |
| 6,684,091 B2 | 1/2004 | Parker |
| 6,687,620 B1 | 2/2004 | Haaland et al. |
| 6,690,466 B2 | 2/2004 | Miller et al. |
| 6,694,157 B1 | 2/2004 | Stone et al. |
| 6,697,655 B2 | 2/2004 | Sueppel et al. |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |
| 6,708,049 B1 | 3/2004 | Berson et al. |
| 6,711,503 B2 | 3/2004 | Haaland |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,705 B2 | 4/2004 | Mills |
| 6,720,734 B2 | 4/2004 | Norris |
| 6,721,582 B2 | 4/2004 | Trepagnier et al. |
| 6,721,584 B2 | 4/2004 | Baker, Jr. et al. |
| 6,721,585 B1 | 4/2004 | Parker |
| 6,725,074 B1 | 4/2004 | Kastle |
| 6,725,075 B2 | 4/2004 | Al-Ali |
| 6,726,634 B2 | 4/2004 | Freeman |
| 6,728,560 B2 | 4/2004 | Kollias et al. |
| 6,735,459 B2 | 5/2004 | Parker |
| 6,741,875 B1 | 5/2004 | Pawluczyk et al. |
| 6,741,876 B1 | 5/2004 | Scecina et al. |
| 6,743,172 B1 | 6/2004 | Blike |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,788,849 B1 | 9/2004 | Pawluczyk |
| 6,792,300 B1 | 9/2004 | Diab et al. |
| 6,800,373 B2 | 10/2004 | Corczyca |
| 6,801,797 B2 | 10/2004 | Mannheimer et al. |
| 6,801,799 B2 | 10/2004 | Mendelson |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,829,501 B2 | 12/2004 | Nielsen et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,842,702 B2 | 1/2005 | Haaland et al. |
| 6,845,256 B2 | 1/2005 | Chin et al. |
| 6,847,835 B1 | 1/2005 | Yamanishi |
| 6,861,641 B1 | 1/2005 | Adams |
| 6,850,787 B2 | 2/2005 | Weber et al. |
| 6,850,788 B2 | 2/2005 | Al-Ali |

(56) References Cited

U.S. PATENT DOCUMENTS

| | | |
|---|---|---|
| 6,852,083 B2 | 2/2005 | Caro et al. |
| 6,861,639 B2 | 3/2005 | Al-Ali |
| 6,869,402 B2 | 3/2005 | Arnold |
| 6,882,874 B2 | 4/2005 | Huiku |
| 6,898,452 B2 | 5/2005 | Al-Ali et al. |
| 6,912,049 B2 | 6/2005 | Pawluczyk et al. |
| 6,917,422 B2 | 7/2005 | Samsoondar et al. |
| 6,919,566 B1 | 7/2005 | Cadell |
| 6,920,345 B2 | 7/2005 | Al-Ali et al. |
| 6,921,367 B2 | 7/2005 | Mills |
| 6,922,645 B2 | 7/2005 | Haaland et al. |
| 6,928,311 B1 | 8/2005 | Pawluczyk et al. |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,944,487 B2 | 9/2005 | Maynard et al. |
| 6,950,687 B2 | 9/2005 | Al-Ali |
| 6,956,572 B2 | 10/2005 | Zaleski |
| 6,961,598 B2 | 11/2005 | Diab |
| 6,970,792 B1 | 11/2005 | Diab |
| 6,975,891 B2 | 12/2005 | Pawluczyk |
| 6,979,812 B2 | 12/2005 | Al-Ali |
| 6,985,764 B2 | 1/2006 | Mason et al. |
| 6,987,994 B1 | 1/2006 | Mortz |
| 6,993,371 B2 | 1/2006 | Kiani et al. |
| 6,996,427 B2 | 2/2006 | Ali et al. |
| 6,999,904 B2 | 2/2006 | Weber et al. |
| 7,001,337 B2 | 2/2006 | Dekker |
| 7,003,338 B2 | 2/2006 | Weber et al. |
| 7,003,339 B2 | 2/2006 | Diab et al. |
| 7,006,856 B2 | 2/2006 | Baker, Jr. et al. |
| 7,015,451 B2 | 2/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,080 B2 | 11/2007 | Acosta et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al-Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| 7,670,726 B2 | 3/2010 | Lu |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |

(56) References Cited

U.S. PATENT DOCUMENTS

| | | |
|---|---|---|
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,116,837 B2 * | 2/2012 | Huang ............... A61B 5/14551 600/310 |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Merritt et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, Iii et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali et al. |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Al-Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |

(56) References Cited

U.S. PATENT DOCUMENTS

| | | |
|---|---|---|
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali et al. |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,994 B2 * | 2/2017 | McCutcheon ..... A61B 5/14551 |
| 9,560,996 B2 | 2/2017 | Kiani |
| 9,560,998 B2 | 2/2017 | Al-Ali et al. |
| 2001/0044700 A1 | 11/2001 | Kobayashi et al. |
| 2001/0045532 A1 | 11/2001 | Schulz et al. |
| 2002/0021269 A1 | 2/2002 | Rast |
| 2002/0026107 A1 | 2/2002 | Kiani et al. |
| 2002/0035318 A1 | 3/2002 | Mannheimer et al. |
| 2002/0038078 A1 | 3/2002 | Ito |
| 2002/0038081 A1 | 3/2002 | Fein et al. |
| 2002/0051290 A1 | 5/2002 | Hannington |
| 2002/0059047 A1 | 5/2002 | Haaland |
| 2002/0082488 A1 | 6/2002 | Al-Ali et al. |
| 2002/0095076 A1 | 7/2002 | Krausman et al. |
| 2002/0095078 A1 | 7/2002 | Mannheimer et al. |
| 2002/0111748 A1 | 8/2002 | Kobayashi et al. |
| 2002/0115919 A1 | 8/2002 | Al-Ali |
| 2002/0154665 A1 | 10/2002 | Funabashi et al. |
| 2002/0156353 A1 | 10/2002 | Larson |
| 2002/0159002 A1 | 10/2002 | Chang |
| 2002/0161291 A1 | 10/2002 | Kiani et al. |
| 2002/0165440 A1 | 11/2002 | Mason et al. |
| 2002/0183819 A1 | 12/2002 | Struble |
| 2002/0198442 A1 | 12/2002 | Rantala et al. |
| 2003/0045784 A1 | 3/2003 | Palatnik et al. |
| 2003/0045785 A1 | 3/2003 | Diab et al. |
| 2003/0049232 A1 | 3/2003 | Page et al. |
| 2003/0109775 A1 | 6/2003 | O'Neil et al. |
| 2003/0116769 A1 | 6/2003 | Song et al. |
| 2003/0117296 A1 | 6/2003 | Seely |
| 2003/0120160 A1 | 6/2003 | Yarita |
| 2003/0120164 A1 | 6/2003 | Nielsen et al. |
| 2003/0135099 A1 | 7/2003 | Al-Ali |
| 2003/0139657 A1 | 7/2003 | Solenberger |
| 2003/0160257 A1 | 8/2003 | Bader et al. |
| 2003/0195402 A1 | 10/2003 | Fein et al. |
| 2004/0006261 A1 | 1/2004 | Swedlow et al. |
| 2004/0033618 A1 | 2/2004 | Haass et al. |
| 2004/0034898 A1 | 2/2004 | Al-Ali et al. |
| 2004/0059209 A1 | 3/2004 | Al-Ali et al. |
| 2004/0064259 A1 | 4/2004 | Haaland et al. |
| 2004/0081621 A1 | 4/2004 | Arndt et al. |
| 2004/0092805 A1 | 5/2004 | Yarita |
| 2004/0133087 A1 | 7/2004 | Al-Ali et al. |
| 2004/0138538 A1 | 7/2004 | Stetson |
| 2004/0138540 A1 | 7/2004 | Baker, Jr. et al. |
| 2004/0147822 A1 | 7/2004 | Al-Ali et al. |
| 2004/0147823 A1 | 7/2004 | Kiani et al. |
| 2004/0158134 A1 | 8/2004 | Diab et al. |
| 2004/0158135 A1 | 8/2004 | Baker, Jr. et al. |
| 2004/0158162 A1 | 8/2004 | Narimatsu |

(56) References Cited

U.S. PATENT DOCUMENTS

| | | |
|---|---|---|
| 2004/0162472 A1 | 8/2004 | Berson et al. |
| 2004/0167382 A1 | 8/2004 | Gardner et al. |
| 2004/0171940 A1 | 9/2004 | Narimatsu |
| 2004/0176670 A1 | 9/2004 | Takamura et al. |
| 2004/0181134 A1 | 9/2004 | Baker, Jr. et al. |
| 2004/0199063 A1 | 10/2004 | O'Neil et al. |
| 2004/0204639 A1 | 10/2004 | Casciani et al. |
| 2004/0204868 A1 | 10/2004 | Maynard et al. |
| 2004/0229391 A1 | 11/2004 | Ohya et al. |
| 2004/0262046 A1 | 12/2004 | Simon et al. |
| 2004/0267103 A1 | 12/2004 | Li et al. |
| 2004/0267140 A1 | 12/2004 | Ito et al. |
| 2005/0011488 A1 | 2/2005 | Al-Ali et al. |
| 2005/0043902 A1 | 2/2005 | Haaland et al. |
| 2005/0049469 A1 | 3/2005 | Aoyagi et al. |
| 2005/0054908 A1 | 3/2005 | Blank et al. |
| 2005/0070773 A1 | 3/2005 | Chin et al. |
| 2005/0070775 A1 | 3/2005 | Chin et al. |
| 2005/0075546 A1 | 4/2005 | Samsoondar et al. |
| 2005/0085735 A1 | 4/2005 | Baker, Jr. et al. |
| 2005/0124871 A1 | 6/2005 | Baker, Jr. et al. |
| 2005/0143634 A1 | 6/2005 | Baker, Jr. et al. |
| 2005/0143943 A1 | 6/2005 | Brown |
| 2005/0148834 A1 | 7/2005 | Hull et al. |
| 2005/0184895 A1 | 8/2005 | Petersen et al. |
| 2005/0187446 A1 | 8/2005 | Nordstrom et al. |
| 2005/0187447 A1 | 8/2005 | Chew et al. |
| 2005/0187448 A1 | 8/2005 | Petersen et al. |
| 2005/0187449 A1 | 8/2005 | Chew et al. |
| 2005/0187450 A1 | 8/2005 | Chew et al. |
| 2005/0187452 A1 | 8/2005 | Petersen et al. |
| 2005/0187453 A1 | 8/2005 | Petersen et al. |
| 2005/0197549 A1 | 9/2005 | Baker, Jr. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0207943 A1 | 9/2005 | Puzey |
| 2005/0209515 A1 | 9/2005 | Hockersmith et al. |
| 2005/0228253 A1 | 10/2005 | Debreczeny |
| 2005/0250997 A1 | 11/2005 | Takedo et al. |
| 2006/0030764 A1 | 2/2006 | Porges et al. |
| 2006/0210120 A1 | 9/2006 | Rowe et al. |
| 2006/0211922 A1 | 9/2006 | Al-Ali et al. |
| 2006/0211923 A1 | 9/2006 | Al-Ali et al. |
| 2006/0211924 A1 | 9/2006 | Smith et al. |
| 2006/0211925 A1 | 9/2006 | Lamego et al. |
| 2006/0211932 A1 | 9/2006 | Al-Ali et al. |
| 2006/0226992 A1 | 10/2006 | Al-Ali et al. |
| 2006/0229509 A1 | 10/2006 | Al-Ali et al. |
| 2006/0238358 A1 | 10/2006 | Al-Ali et al. |
| 2006/0241358 A1 | 10/2006 | Al-Ali et al. |
| 2006/0241363 A1 | 10/2006 | Al-Ali et al. |
| 2006/0264718 A1 | 11/2006 | Ruchti et al. |
| 2007/0093701 A1 | 4/2007 | Myers |
| 2007/0149864 A1 | 6/2007 | Laakkonen |
| 2007/0129616 A1 | 7/2007 | Rantala |
| 2007/0185397 A1 | 8/2007 | Govari et al. |
| 2007/0282478 A1 | 12/2007 | Al-Ali et al. |
| 2008/0281174 A1 | 11/2008 | Dietiker |
| 2009/0163775 A1 | 6/2009 | Barrett et al. |
| 2009/0247849 A1 | 10/2009 | McCutcheon et al. |
| 2009/0247924 A1 | 10/2009 | Harima et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0288383 A1 | 11/2011 | Diab |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0172701 A1 | 7/2013 | Smith |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali |
| 2013/0317370 A1 | 11/2013 | Dalvi et al. |
| 2013/0336481 A1 | 11/2013 | Shakespeare et al. |
| 2013/0324808 A1 | 12/2013 | Al-Ali et al. |
| 2013/0330092 A1 | 12/2013 | Amit et al. |
| 2013/0330098 A1 | 12/2013 | Chae et al. |
| 2013/0330099 A1 | 12/2013 | Gutierrez et al. |
| 2013/0331660 A1 | 12/2013 | Al-Ali et al. |
| 2013/0331670 A1 | 12/2013 | Kiani |
| 2013/0333440 A1 | 12/2013 | Hedtke |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali |
| 2014/0142401 A1 | 5/2014 | Al-Ali et al. |
| 2014/0142402 A1 | 5/2014 | Al-Ali |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali |
| 2014/0194766 A1 | 7/2014 | Al-Ali et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |

(56) References Cited

U.S. PATENT DOCUMENTS

| | | |
|---|---|---|
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0027456 A1 | 2/2017 | Kinast et al. |
| 2017/0042488 A1 | 2/2017 | Muhsin |

FOREIGN PATENT DOCUMENTS

| | | |
|---|---|---|
| EP | 0 569 670 | 2/1993 |
| EP | 0 529 412 | 3/1993 |
| EP | 0 675 540 | 10/1995 |
| EP | 0 675 541 | 10/1995 |
| EP | 1 080 683 | 3/2001 |
| EP | 1 207 536 | 5/2002 |
| EP | 1 895 892 | 5/2010 |
| EP | 2 305 104 | 4/2011 |
| EP | 2 476 369 | 7/2012 |
| JP | 61-28172 | 2/1986 |
| JP | 62-000324 | 1/1987 |
| JP | 63-275327 | 11/1988 |
| JP | 64-500495 | 2/1989 |
| JP | 2-126829 | 5/1990 |
| JP | 2-145457 | 12/1990 |
| JP | 03-252604 | 11/1991 |
| JP | 05-200017 | 8/1993 |
| JP | 05-207993 | 8/1993 |
| JP | 6-505903 | 7/1994 |
| JP | 6-237013 | 8/1994 |
| JP | 7-281618 | 10/1995 |
| JP | 07-325546 | 12/1995 |
| JP | 09-503402 | 4/1997 |
| JP | 9-192120 | 7/1997 |
| JP | 09-308623 | 12/1997 |
| JP | 10-500026 | 1/1998 |
| JP | 10-216112 | 8/1998 |
| JP | 10-509352 | 9/1998 |
| JP | 10-269344 A | 10/1998 |
| JP | 10-295676 | 11/1998 |
| JP | 10-305026 | 11/1998 |
| JP | 63-275327 | 11/1998 |
| JP | 11-037932 | 2/1999 |
| JP | 11-163412 | 6/1999 |
| JP | 11-164826 | 6/1999 |
| JP | 11-506834 | 6/1999 |
| JP | 11-183377 | 7/1999 |
| JP | 11-508691 | 7/1999 |
| JP | 2000-116625 | 4/2000 |
| JP | 2000-199880 | 7/2000 |
| JP | 2002-150821 | 5/2002 |
| JP | 2002-516689 | 6/2002 |
| JP | 2002-228579 | 8/2002 |
| JP | 2002-525151 | 8/2002 |
| JP | 2002-315739 | 10/2002 |
| JP | 2002-352609 | 12/2002 |
| JP | 2003-507718 | 2/2003 |
| JP | 2003-084108 | 3/2003 |
| JP | 2003-521985 | 7/2003 |
| JP | 2004-070179 | 3/2004 |
| JP | 2004-510467 | 4/2004 |
| JP | 2004-173866 | 6/2004 |
| JP | 2004-226277 | 8/2004 |
| JP | 2004-296736 | 10/2004 |
| JP | 2004-532526 | 10/2004 |
| JP | 2004-327760 | 11/2004 |
| JP | 2005-501589 | 1/2005 |
| JP | 2005-253478 | 9/2005 |
| JP | 2008-505706 | 2/2008 |
| JP | 4879913 | 12/2011 |
| JP | 2012-110746 | 6/2012 |
| JP | 5096174 | 9/2012 |
| JP | 5328159 | 8/2013 |
| JP | 5456976 | 1/2014 |
| WO | WO 88/01150 | 2/1988 |
| WO | WO 88/002020 | 2/1988 |

(56) References Cited

FOREIGN PATENT DOCUMENTS

| | | |
|---|---|---|
| WO | WO 92/16142 | 10/1992 |
| WO | WO 95/05621 | 2/1995 |
| WO | WO 95/16387 | 6/1995 |
| WO | WO 96/013208 | 5/1996 |
| WO | WO 96/41138 | 12/1996 |
| WO | WO 97/01985 | 1/1997 |
| WO | WO 98/43071 | 10/1998 |
| WO | WO 00/18290 | 4/2000 |
| WO | WO 00/42911 | 7/2000 |
| WO | WO 00/59374 | 10/2000 |
| WO | WO 01/13790 | 3/2001 |
| WO | WO 01/30414 | 5/2001 |
| WO | WO 01/058347 | 8/2001 |
| WO | WO 02/017780 | 3/2002 |
| WO | WO 02/26123 | 4/2002 |
| WO | WO 02/089664 | 3/2003 |
| WO | WO 03/020129 | 3/2003 |
| WO | WO 03/068060 | 8/2003 |
| WO | WO 03/077761 | 9/2003 |
| WO | WO 04/034898 | 4/2004 |
| WO | WO 04/038801 | 5/2004 |
| WO | WO 05/004712 | 1/2005 |
| WO | WO 05/011488 | 2/2005 |
| WO | WO 06/094168 | 9/2006 |
| WO | WO 06/115580 | 11/2006 |

OTHER PUBLICATIONS

Burritt, Mary F.; Current Analytical Approaches to Measuring Blood Analytes; vol. 36; No. 8(B); 1990.
International Search Report for EP Appl. No. 10191029 dated May 25, 2012 in 5 pages.
European Examination Report, re EP Application No. 12163719.3, dated Feb. 6, 2013.
European Extended Search Report of European Application No. 12163719.3, dated Jun. 18, 2012, in 6 pages.
European Extended Search Report, re EP Application No. 12163719.3, dated Jun. 18, 2012.
European Office Action re EP Application No. 06 736 799.5, dated Nov. 30, 2012.
European Search Report, re EP Application No. 10 19 1029, dated Jun. 5, 2012.
European Examination Report dated Apr. 1, 2010, re EP App. No. 08 7 44 412.1-2319.
European Examination Report dated Mar. 18, 2011, re EP App. No. 08 7 44 412.1-2319.
European Examination Report dated Sep. 2, 2010, re EP App. No. 08 7 44 412.1-2319.
European Extended Search Report re EPO App. No. 10162402.1, SR dated Aug. 9, 2010.
European Office Action re EPO App. No. 10162402.1, SR dated Mar. 4, 2013.
Hall, et al., Jeffrey W.; Near-Infrared Spectrophotometry: A New Dimension in Clinical Chemistry; vol. 38; No. 9; 1992.
International Preliminary Report on Patentability for PCT/US2010/058981 issued Jun. 5, 2012, dated Jun. 14, 2012.
International Search Report for PCT/US2006/007516, dated Jan. 11, 2007, in 4 pages.
Japanese Office Action (Notice of Reasons for Rejection) re JP App. No. 2007-558246, dated Jun. 28, 2011.
Japanese Office Action (Reasons for Rejection) re JP App. No. 2007-558246, dated Nov. 1, 2011.
Japanese Office Action (Official Inquiry) re JP App. No. 2007-558246, dated Dec. 11, 2012.
Japanese Office Action, re JP Application No. 2012-045419, dated Jun. 26, 2012.
Japanese Office Action re JP Application No. JP 2007-558208, dated Aug. 23, 2011.
Japanese Office Action re JP Application No. JP 2007-558208, dated May 8, 2012.
Japanese First Office Action (Notice of Reasons for Rejection), re JP App. No. 2007-558247, dated Jun. 28, 2011.
Japanese Office Action (Notice of Allowance), re JP App. No. 2007-558247, dated Oct. 24, 2011.
Japanese Office Action (Decision of Rejection), re JP Application No. JP 2007-558328, dated Nov. 20, 2012.
Japanese Office Action (Decision of Rejection), re JP Application No. JP 2007-558328, dated Jun. 25, 2013.
Japanese Office Action, Decision of Rejection of Amendment, re JP Application No. JP 2007-558328, dated Jun. 25, 2013.
Japanese Office Action (Notice of Reasons for Rejection), re JP App. No. 2007-558238, dated Jun. 28, 2011.
Japanese Office Action (Notice of Reasons for Rejection), re JP App. No. 2007-558238, dated Jun. 26, 2012.
Japanese Office Action (Official Inquiry), re JP App. No. 2007-558238/Appeal No. 2012- 004053, dated Dec. 11, 2012.
Japanese Office Action re JP Application No. JP 2007-558248, dated Nov. 8, 2011.
Japanese Office Action re JP Application No. JP 2007-558248, dated Nov. 27, 2012.
Japanese First Office Action (Notice of Reasons for Rejection), re JP App. No. 2007-558207, dated Jun. 28, 2011.
Japanese Office Action, re JP Application No. 2007-558237, dated Aug. 2, 2011.
Japanese Office Action, re JP Application No. JP 2007-558237, dated Oct. 16, 2012.
Japanese Office Action re JP Application No. 2007-558209, dated Oct. 25, 2011.
Japanese Office Action re JP Application No. 2007-558209, dated Oct. 30, 2012.
Japanese Office Action re JP Application No. 2007-558245, dated Oct. 25, 2011.
Japanese Office Action re JP Application No. 2007-558245, dated Jan. 15, 2013.
Japanese Office Action re JP Application No. 2007-558245, dated Oct. 29, 2013.
Japanese Office Action re JP Application No. 2007-558249, dated Jul. 13, 2011.
Japanese Office Action re JP Application No. 2007-558249, dated Nov. 8, 2011.
Japanese Final Office Action re Amendments re JP Application No. 2007-558249, dated Apr. 17, 2012.
Japanese Office Action re JP Application No. 2007-558249, dated Aug. 28, 2012.
Kuenstner, et al., J. Todd; Measurement of Hemoglobin in Unlysed Blood by Near-Infrared Spectroscopy; vol. 48; No. 4, 1994.
Manzke, et al., B., Multi Wavelength Pulse OXimetry in the Measurement of Hemoglobin Fractions; vol. 2676, date unknown.
Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.
Patent Cooperation Treaty (PCT) International Search Report, PCT/US 2006/007389; dated Jul. 17, 2006; pp. 1-9.
PCT International Search Report; PCT/US 2006/007389; dated Jul. 17, 2006; pp. 1-9.
PCT International Search Report; PCT-US2006-007387; dated Jul. 17, 2006; pp. 1-9.
PCT International Search Report; PCT-US2006-007388; dated Jul. 17, 2006; pp. 1-9.
PCT International Search Report; PCT-US2006-007506; dated Jul. 17, 2006; pp. 1-10.
PCT International Search Report; PCT-US2006-007536; dated Jul. 17, 2006; pp. 1-9.
PCT International Search Report; PCT-US2006-007537; dated Jul. 17, 2006; pp. 1-10.
PCT International Search Report; PCT-US2006-007538; dated Jul. 17, 2006; pp. 1-9.
PCT International Search Report; PCT/US2006/007539; dated Jul. 17, 2006; pp. 1-9.
PCT International Search Report; PCT-US2006-007540; dated Jul. 17, 2006; pp. 1-9.

(56) References Cited

OTHER PUBLICATIONS

PCT International Search Report; PCT-US2006-007958; dated Jul. 17, 2006; pp. 1-8.
PCT International Search Report for PCT/US2006/077516, dated Jan. 11, 2007, in 4 pages.
PCT Search Report of International Application No. PCT/US2008/058327, dated Jun. 30, 2009, in 12 pages.
Schmitt, Joseph M.; Simple Photon Diffusion Anaylsis of the Effects of Multiple Scattering on Pulse Oximetry; Mar. 14, 1991; revised Aug. 30, 1991.
Schmitt, Joseph M.; Zhou, Guan-Xiong; Miller, Justin, Measurement of Blood Hematocrit by Dual-wavelength Near-IR Photoplethysmography, published May 1992, Proc. SPIE vol. 1641, p. 150-161, Physiological Monitoring and Early Detection Diagnostic Methods, Thomas S. Mang; Ed. (SPIE homepage), in 12 pages.
Schnapp, et al., L.M.; Pulse Oximetry. Uses and Abuses.; Chest 1990; 98; 1244-1250001 10.1378/Chest.98.5.1244.

\* cited by examiner

PHYSIOLOGICAL MEASUREMENT SYSTEM WITH AUTOMATIC WAVELENGTH ADJUSTMENT

PRIORITY CLAIM TO RELATED PROVISIONAL APPLICATIONS

Any and all applications for which a foreign or domestic priority claim is identified in the Application Data Sheet as filed with the present application are hereby incorporated by reference under 37 CFR 1.57. The present application is a continuation of U.S. patent application Ser. No. 12/949,271, filed Nov. 18, 2010, entitled "PHYSIOLOGICAL MEASUREMENT SYSTEM WITH AUTOMATIC WAVELENGTH ADJUSTMENT," which claims priority benefit under 35 U.S.C. § 119(e) to U.S. Provisional Patent Application Ser. No. 61/264,182, filed Nov. 24, 2009, entitled "PHYSIOLOGICAL MEASUREMENT SYSTEM WITH AUTOMATIC WAVELENGTH ADJUSTMENT," and No. 61/330,253, filed Apr. 30, 2010, entitled "PHYSIOLOGICAL MEASUREMENT SYSTEM WITH AUTOMATIC WAVELENGTH ADJUSTMENT." The present application incorporates the foregoing disclosures herein by reference.

INCORPORATION BY REFERENCE OF COPENDING RELATED APPLICATIONS

The present application is related to the following copending U.S. utility applications:

|   | Application Ser. No. | Filing Date | Title |
|---|---|---|---|
| 1 | 11/367,013 | Mar. 1, 2006 | Multiple Wavelength Sensor Emitters |
| 2 | 11/366,955 | Mar. 1, 2006 | Multiple Wavelength Sensor Equalization |
| 3 | 11/366,209 | Mar. 1, 2006 | Multiple Wavelength Sensor Substrate |
| 4 | 11/366,210 | Mar. 1, 2006 | Multiple Wavelength Sensor Interconnect |
| 5 | 11/366,833 | Mar. 1, 2006 | Multiple Wavelength Sensor Attachment |
| 6 | 11/366,997 | Mar. 1, 2006 | Multiple Wavelength Sensor Drivers |
| 7 | 11/367,034 | Mar. 1, 2006 | Physiological Parameter Confidence Measure |
| 8 | 11/367,036 | Mar. 1, 2006 | Configurable Physiological Measurement System |
| 9 | 11/367,033 | Mar. 1, 2006 | Noninvasive Multi-Parameter Patient Monitor |
| 10 | 11/367,014 | Mar. 1, 2006 | Noninvasive Multi-Parameter Patient Monitor |
| 11 | 11/366,208 | Mar. 1, 2006 | Noninvasive Multi-Parameter Patient Monitor |
| 12 | 12/056,179 | Mar. 26, 2008 | Multiple Wavelength Optical Sensor |
| 13 | 12/082,810 | Apr. 14, 2008 | Optical Sensor Assembly |

The present application incorporates the foregoing disclosures herein by reference.

BACKGROUND

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\varepsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \varepsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve EQS. 1-2 are the number of significant absorbers that are present in the solution.

A practical application of this technique is pulse oximetry, which utilizes a noninvasive sensor to measure oxygen saturation ($SpO_2$) and pulse rate. In general, the sensor has light emitting diodes (LEDs) that transmit optical radiation of red and infrared wavelengths into a tissue site and a detector that responds to the intensity of the optical radiation after absorption (e.g., by transmission or transreflectance) by pulsatile arterial blood flowing within the tissue site. Based on this response, a processor determines measurements for $SpO_2$, pulse rate, and can output representative plethysmographic waveforms. Thus, "pulse oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood. Pulse oximeters capable of reading through motion induced noise are available from Masimo Corporation ("Masimo") of Irvine, Calif. Moreover, portable and other oximeters capable of reading through motion induced noise are disclosed in at least U.S. Pat. Nos. 6,770,028, 6,658,276, 6,157,850, 6,002,952 5,769,785, and 5,758,644, which are owned by Masimo and are incorporated by reference herein. Such reading through motion oximeters have gained rapid acceptance in a wide variety of medical applications, including surgical wards, intensive care and neonatal units, general wards, home care, physical training, and virtually all types of monitoring scenarios.

FIG. 1 illustrates $HbO_2$ (Oxyhemoglobin) and Hb (Hemoglobin) absorption $\mu_a$ versus wavelength. At red and near IR wavelengths below 970 nm, where water has a significant peak, Hb and $HbO_2$ are the only significant absorbers normally present in the blood. Thus, typically only two wavelengths are needed to resolve the concentrations of Hb and $HbO_2$, e.g. a red (RD) wavelength at 660 nm and an infrared (IR) wavelength at 940 nm. In particular, $SpO_2$ is computed based upon a red ratio $Red_{AC}/Red_{DC}$ and an IR ratio $IR_{AC}/IR_{DC}$, which are the AC detector response magnitude at a particular wavelength normalized by the DC detector response at that wavelength. The normalization by the DC detector response reduces measurement sensitivity to variations in tissue thickness, emitter intensity and detector sensitivity, for example. The AC detector response is a plethysmograph, as described above. Thus, the red and IR ratios can be denoted as $NP_{RD}$ and $NP_{IR}$ respectively, where NP stands for "normalized plethysmograph." In pulse oximetry, oxygen saturation is calculated from the ratio $NP_{RD}/NP_{IR}$.

SUMMARY OF THE DISCLOSURE

Embodiments of the disclosure are directed to a physiological measurement system that can automatically adjust the number of wavelengths used based on a sensor signal that is indicative of the optical radiation detected at the sensor after tissue attenuation. In an embodiment, the physiological measurement system performs a calibration process upon power up and/or a first attachment to a tissue site. During the calibration process, the system provides test currents to the light emitting sources in the emitter assembly and examines the sensor signal to determine if the signal quality is sufficient to support the use of a full set of wavelengths. The full set of wavelengths includes eight wavelengths in an embodiment. If it is determined that the signal quality is insufficient to support the full set, a reduced number of wavelengths is used. In an embodiment, the wavelengths at 660 nm and 905 nm, the minimum two wavelengths needed to provide a SpO2 reading, are used in lieu of the full set of wavelengths. In other embodiments, other reduced numbers of wavelengths are used. In other embodiments, the physiological measurement system continually monitors signal quality and automatically adjusts the number of wavelengths used.

DETAILED DESCRIPTION OF THE PREFERRED EMBODIMENTS

In this application, reference is made to many blood parameters. Some references that have common shorthand designations are referenced through such shorthand designations. For example, as used herein, HbCO designates carboxyhemoglobin, HbMet designates methemoglobin, and Hbt designates total hemoglobin. Other shorthand designations such as COHb, MetHb, and tHb are also common in the art for these same constituents. These constituents are generally reported in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

Embodiments of the disclosure are directed to a physiological measurement system that can automatically adjust the number of wavelengths used based on a sensor signal that is indicative of the optical radiation detected at the sensor after tissue attenuation. In various embodiments, the adjustment process utilizes various methods of NP profile comparison to derive a confidence measurement to measure the quality of the signal detected at the sensor. In other embodiments, the system provides test currents to light emitter sources in the emitter assembly and measure sensor signals in response to the light emitted to determine signal quality. If the signal quality is insufficient to support using the full set of wavelengths, the physiological measurement system can switch to using less than the full set of wavelengths.

Example Normalized Plethysmograph (NP) Tissue Profile

Figure 1:
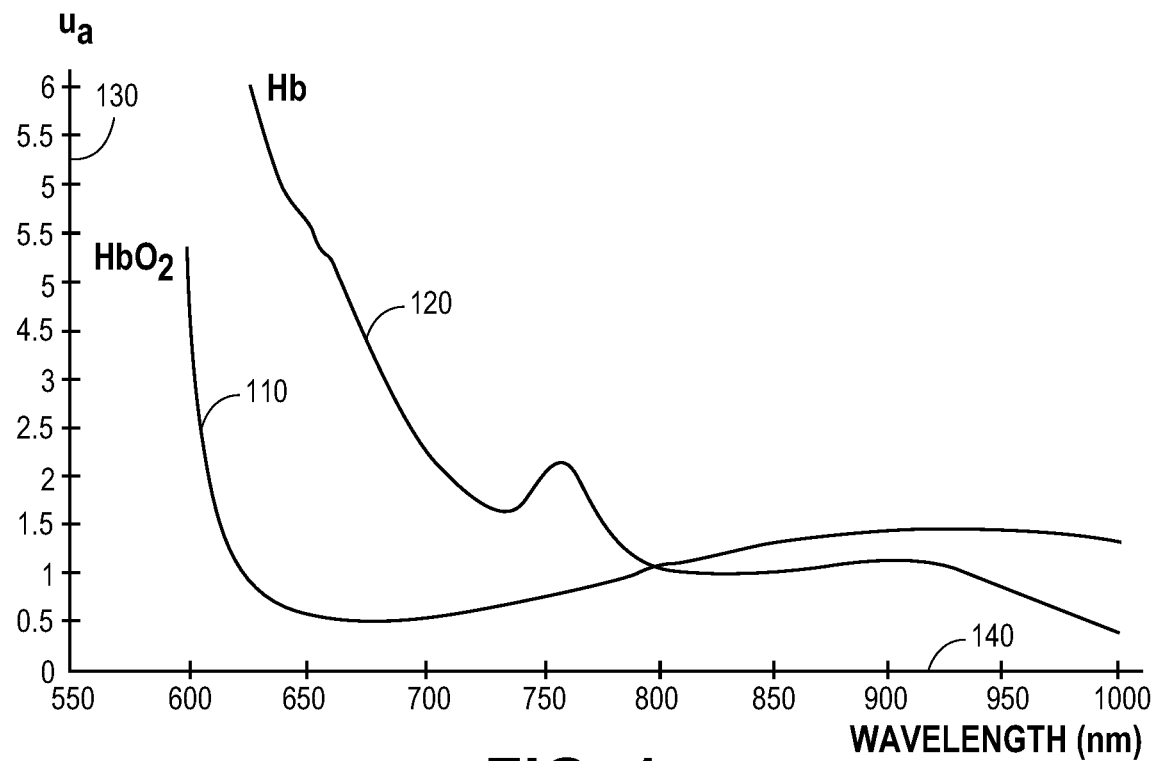
FIG. 1 is a graph of oxyhemoglobin and reduced hemoglobin light absorption versus wavelength across portions of the red and IR spectrum.
Figure 2:
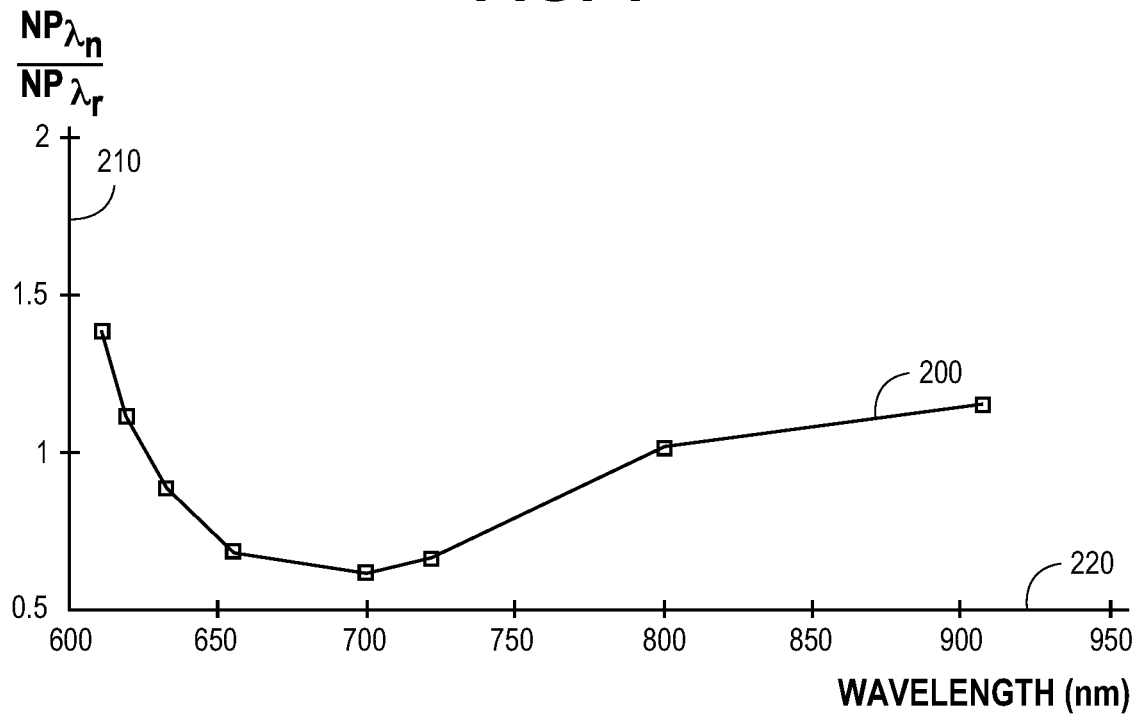
FIG. 2 is a graph of NP ratios versus wavelength illustrating a tissue profile.

FIG. 2 illustrates an example of a "tissue profile" 200 for SpO2=97%. For this example, including FIGS. 7A-7B, below, the sensor emits eight wavelengths (610, 620, 630, 655, 700, 720, 800 and 905 nm). The graph is a plot of NP ratios 210 versus wavelength 220, where the NP ratios are of the form $NP_{\lambda 1}/NP_{\lambda 2}$. This is a generalization to multiple wavelengths of the ratio $NP_{RD}/NP_{IR}$ described above in FIG. 1 for two (red and IR) wavelengths. In order to provide a common scale for these NP ratios, the ratios are calculated with respect to a reference wavelength, λr, which may be any of the available wavelengths. Thus, the plotted NP ratios are denoted $NP_{\lambda,r}/NP_{\lambda,r}$ over the n available wavelengths, including λr. Note that the NP ratio at the reference wavelength is $NP_{\lambda,r}/NP_{\lambda,r}=1$, which is 800 nm in FIG. 2.

As shown in FIG. 2, when a sensor is properly positioned on a tissue site, the detector only receives LED emitted light that has propagated through the tissue site after tissue scattering and absorption. Thus, a tissue profile 200 should reflect the blood constituent absorption characteristics illustrated in FIG. 1, above. For this high oxygen saturation (97%) example, $HbO_2$ is the only significantly absorbing blood constituent and, indeed, the resulting tissue profile 200 is shaped like the $HbO_2$ absorption curve 110 (FIG. 1).

Figure 3A:
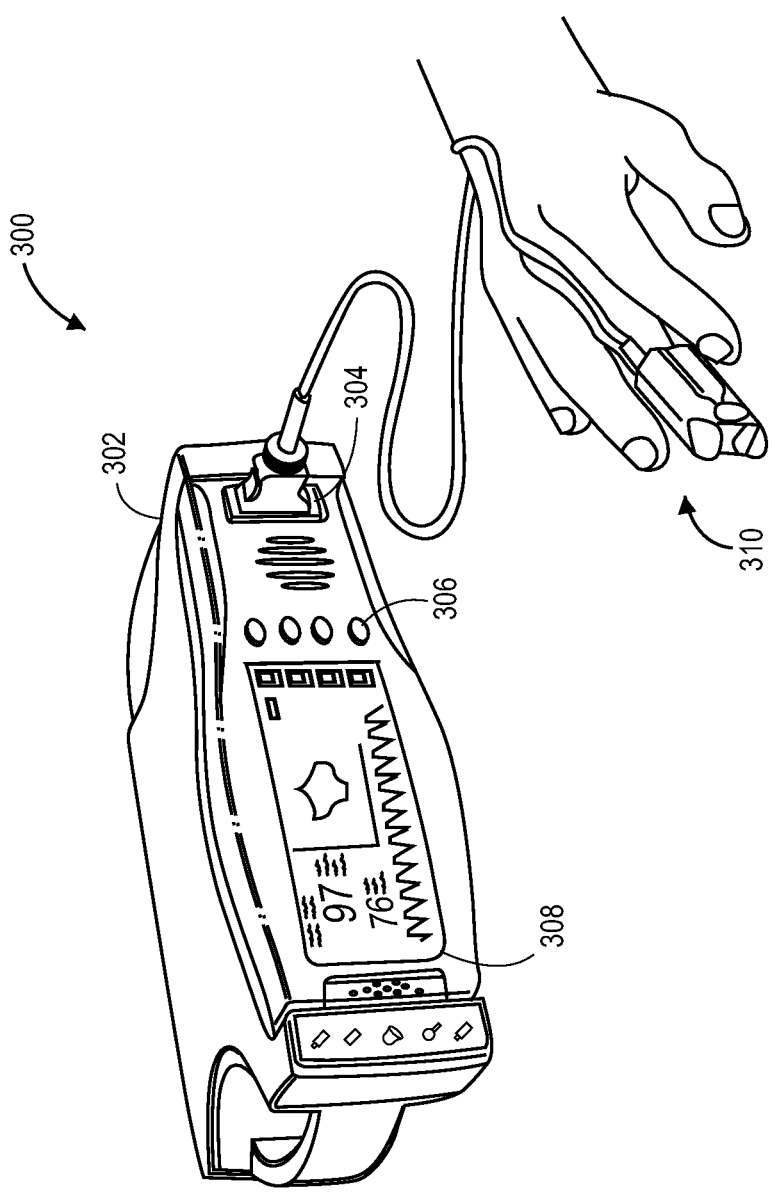
FIG. 3A is a perspective view of a physiological measurement system utilizing a multiple wavelength sensor.

FIG. 3A illustrates an example physiological measurement system 300 that can output and detect wavelength profiles similar to that shown in FIG. 2. In an embodiment, the measurement system 300 includes a monitor 302 and a multiple wavelength sensor assembly 310 with enhanced measurement capabilities as compared with conventional pulse oximetry. The physiological measurement system 300 allows the monitoring of a person, including a patient. In particular, the multiple wavelength sensor assembly 310 allows the measurement of blood constituent and related parameters in addition to oxygen saturation and pulse rate. Alternatively, the multiple wavelength sensor assembly 310 allows the measurement of oxygen saturation and pulse rate with increased accuracy or robustness as compared with conventional pulse oximetry.

In an embodiment, the sensor assembly 310 is configured to plug into a monitor sensor port 304. Monitor keys 306 provide control over operating modes and alarms, to name a few. A display 308 provides readouts of measured parameters, such as oxygen saturation, pulse rate, HbCO and HbMet to name a few.

Figure 3B:
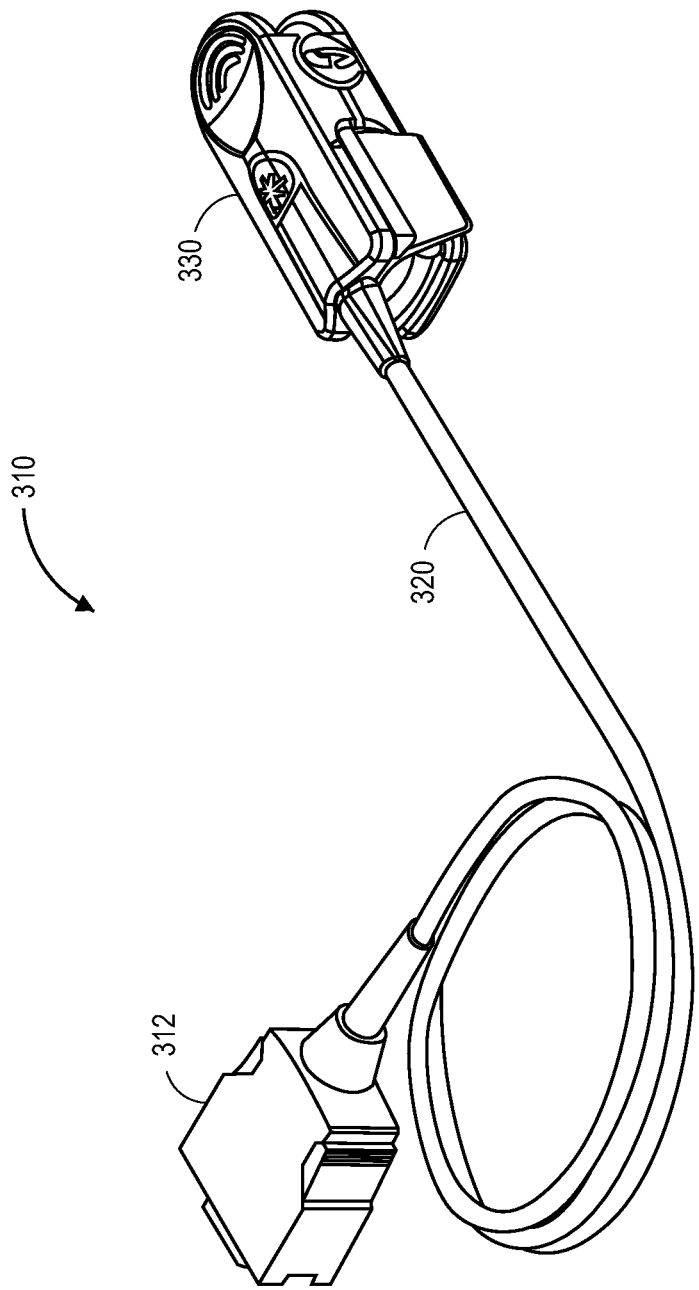
FIG. 3B is a perspective view of a multiple wavelength sensor embodiment.

FIG. 3B illustrates a multiple wavelength sensor assembly 310 having a sensor 330 adapted to attach to a tissue site, a sensor cable 320 and a monitor connector 312. In an embodiment, the sensor 330 is incorporated into a reusable finger clip adapted to removably attach to, and transmit light through, a fingertip. The sensor cable 320 and monitor connector 312 are integral to the sensor 330, as shown. In alternative embodiments, the sensor 330 may be configured separately from the cable 320 and connector 312.

Figure 4A:
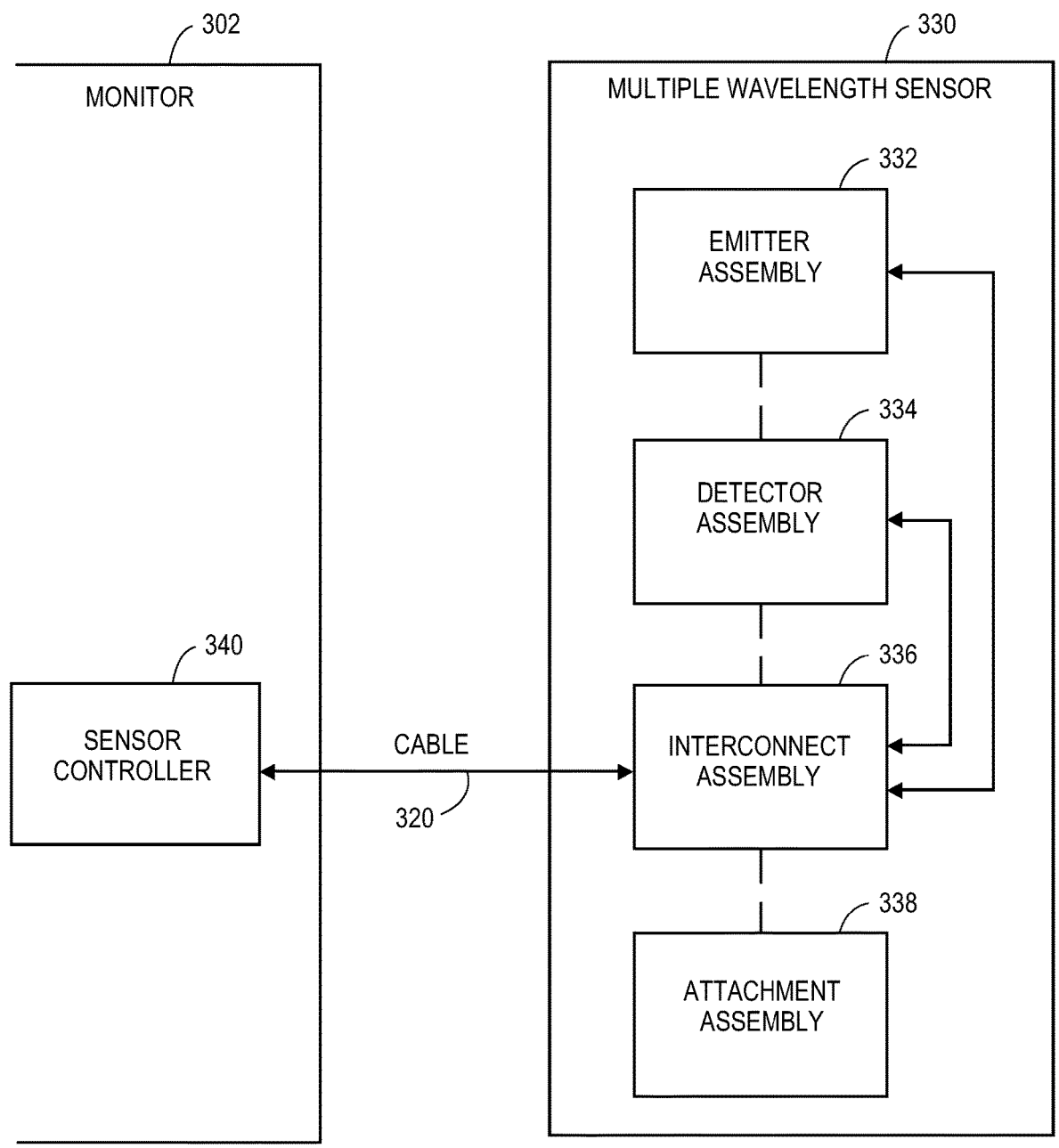
FIG. 4A is a general block diagram of a multiple wavelength sensor and sensor controller.

FIG. 4A illustrates the sensor 330 having an emitter assembly 332, a detector assembly 334, an interconnect assembly 336 and an attachment assembly 338. The emitter assembly 332 responds to drive signals received from a sensor controller 340 in the monitor 302 via the cable 320 so as to transmit optical radiation having a plurality of wavelengths into a tissue site. The detector assembly 334 provides a sensor signal to the monitor 302 via the cable 320 in response to optical radiation received after attenuation by the tissue site. The interconnect assembly 336 provides electrical communication between the cable 320 and both the emitter assembly 332 and the detector assembly 334. The attachment assembly 338 attaches the emitter assembly 332 and detector assembly 334 to a tissue site, as described above. Additional details of the detector assembly 334, the interconnect assembly 336 and the attachment assembly 338 are further described in the above-referenced app. Ser. No. 11/367,013, filed Mar. 1, 2006, entitled "Multiple Wavelength Sensor Emitters," which has been incorporated by reference above. The emitter assembly 332 will be described in further details below.

Figure 4B:
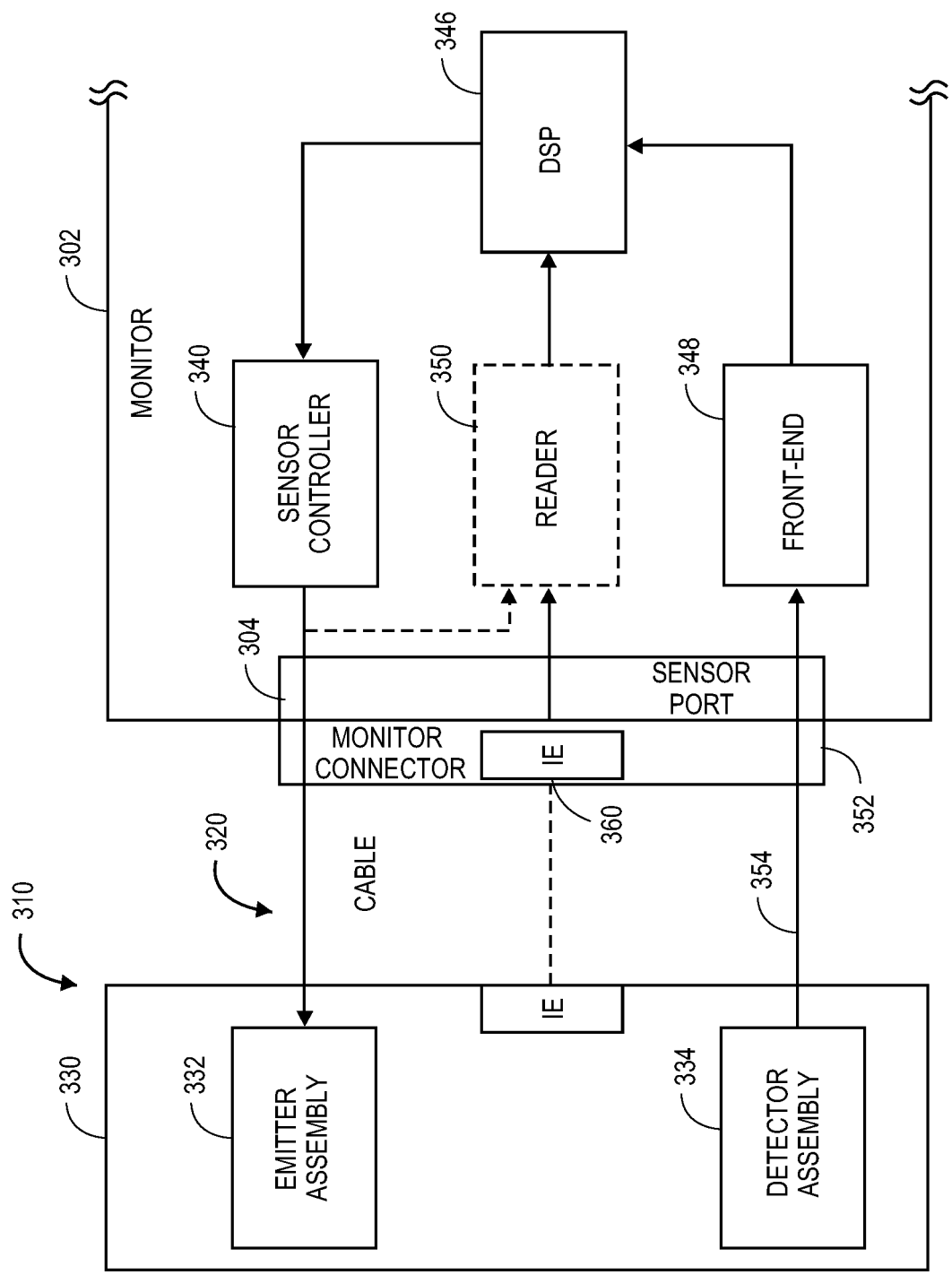
FIG. 4B is a general block diagram of a monitor and a sensor.

FIG. 4B illustrates a monitor 302 and a corresponding sensor assembly 310, as described generally with respect to FIGS. 3A, 3B and 4A above. As discussed above, the sensor assembly 310 houses the emitter assembly 332 having emitters. In an embodiment, the emitter assembly 332 is responsive to drivers within a sensor controller 340 so as to transmit optical radiation into a tissue site. The sensor 330 also houses a detector assembly 334 that provides a sensor signal 354 responsive to the optical radiation after tissue attenuation. In an embodiment, the sensor signal 354 is filtered, amplified, sampled and digitized by a front-end 348 and input to a DSP (digital signal processor) 346, which also commands the sensor controller 340. The sensor cable 320 electrically communicates drive signals from the sensor controller 340 to the emitter assembly 332 and a sensor signal 354 from the detector assembly 334 to a front-end 348. The sensor cable 320 has a monitor connector 352 that plugs into a monitor sensor port 304.

In an embodiment, the DSP 346 processes the incoming digitalized sensor signal 354 and determines whether the signal quality requires a change to the number of wavelengths that are active in the emitter assembly. In an embodiment, the DSP 346 includes methods and components for determining signal quality as shown in FIGS. 8A-12, as will be further described below.

In an embodiment, the monitor 302 also has a reader 350 capable of obtaining information from an information element (IE) 360 in the sensor assembly and transferring that information to the DSP 346, to another processor or component within the monitor 302, or to an external component or device that is at least temporarily in communication with the monitor 302. In an alternative embodiment, the reader function is incorporated within the DSP 346, utilizing one or more of DSP I/O, ADC, DAC features and corresponding processing routines, as examples. Additional details and alternate embodiments for components shown in FIG. 4B are further described in FIGS. 41-46 of the above-referenced app. Ser. No. 11/367,013, filed Mar. 1, 2006, entitled "Multiple Wavelength Sensor Emitters."

In an embodiment, the monitor connector 352 houses the information element 360, which may be a memory device or other active or passive electrical component. In a particular embodiment, the information element 360 is an EPROM, or other programmable memory, or an EEPROM, or other reprogrammable memory, or both. In an alternative embodiment, the information element 360 is housed within the sensor 330, or an information element 360 is housed within both the monitor connector 352 and the sensor 330. In yet another embodiment, the emitter assembly 332 has an information element 360, which is read in response to one or more drive signals from the sensor controller 340. In a further embodiment, a memory information element is incorporated into the emitter array 400 (FIG. 5A) and has characterization information relating to the LEDs 490 (FIG. 5B). In one advantageous embodiment, trend data relating to slowly varying parameters, such as perfusion index, HbCO or METHb, to name a few, are stored in an IE memory device, such as EEPROM.

Emitter Assembly

Figure 4C:
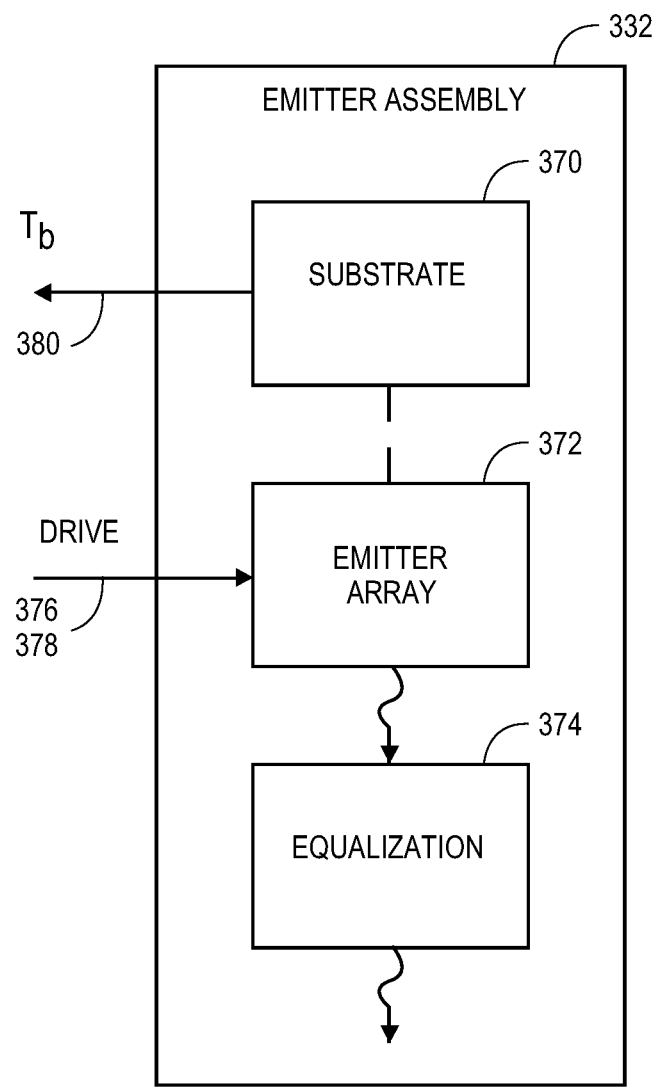
FIG. 4C is a general block diagram of an emitter assembly.

FIG. 4C illustrates an emitter assembly 332 having an emitter array 372, a substrate 370 and equalization 374. The emitter array 372 has multiple light emitting sources, each activated by addressing at least one row and at least one column of an electrical grid. The light emitting sources are capable of transmitting optical radiation having multiple wavelengths. The equalization 374 accounts for differences in tissue attenuation of the optical radiation across the multiple wavelengths so as to at least reduce wavelength-dependent variations in detected intensity. The substrate 370 provides a physical mount for the emitter array and emitter-related equalization and a connection between the emitter array and the interconnection assembly. Advantageously, the substrate 370 also provides a bulk temperature measurement so as to calculate the operating wavelengths for the light emitting sources. The equalization 374 and the substrate 370 are described in further detail in above-referenced app. Ser. No. 11/367,013, filed Mar. 1, 2006, entitled "Multiple Wavelength Sensor Emitters," which has been incorporated by reference above.

Emitter Array

Figure 5A:
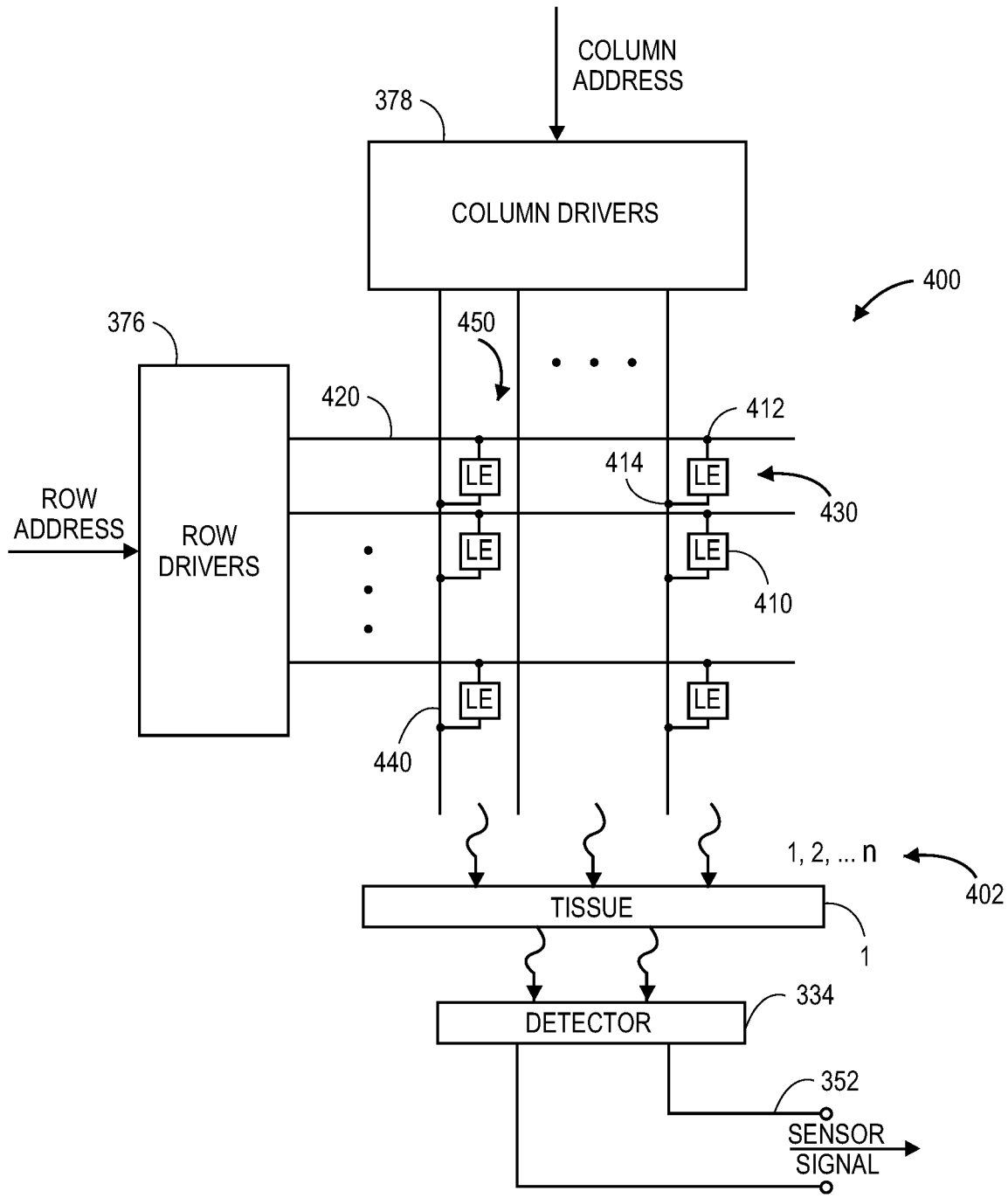
FIG. 5A is a general block diagram of an emitter array.
Figure 5B:
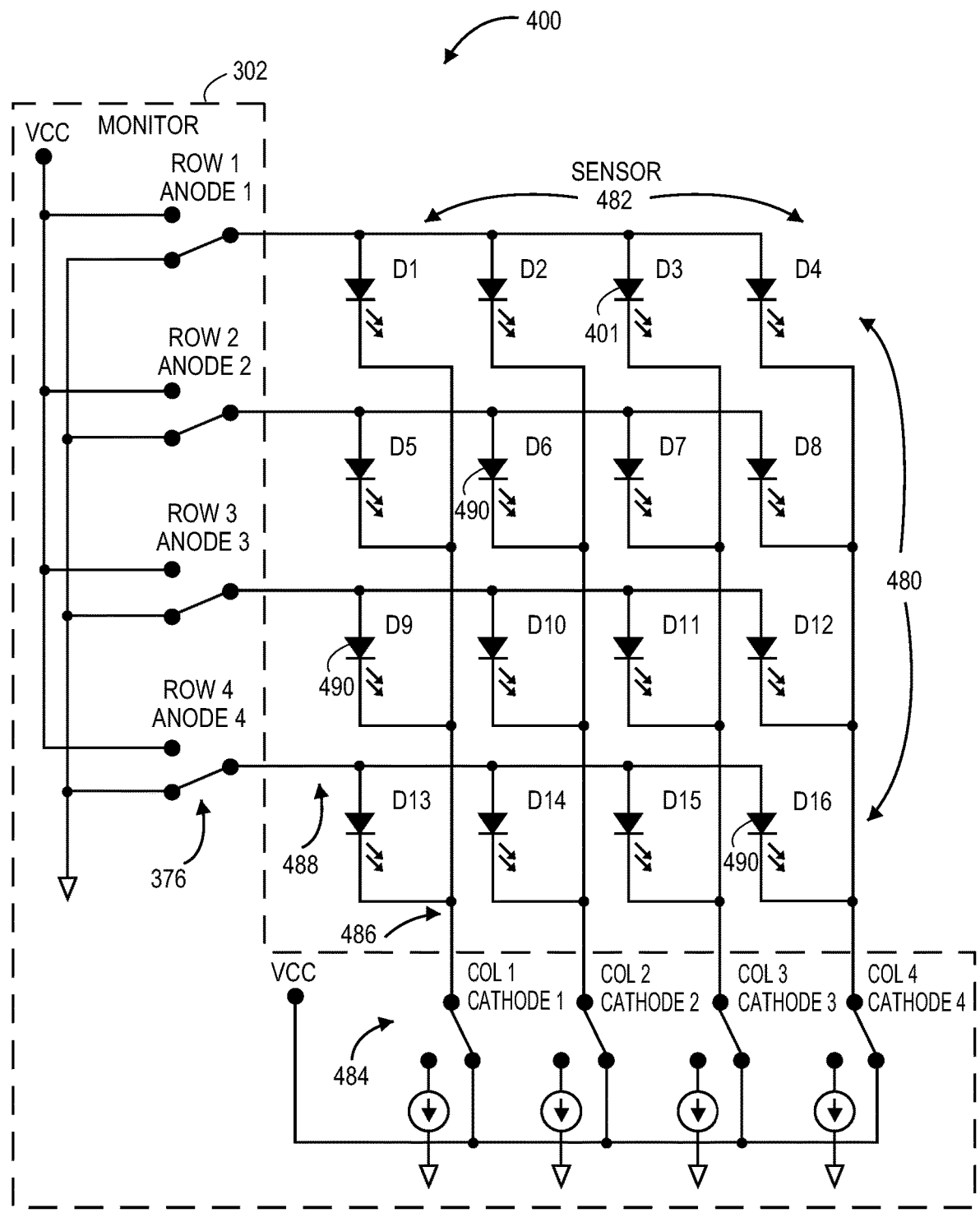
FIG. 5B is a schematic diagram of an emitter array embodiment.

FIG. 5A illustrates an emitter array 400 having multiple light emitters (LE) 410 capable of emitting light 402 having multiple wavelengths into a tissue site 1. The emitter array 400 emits optical radiation having multiple wavelengths of predetermined nominal values, advantageously allowing multiple parameter measurements. In particular, the emitter array 400 has multiple light emitting diodes (LEDs) 410 that are physically arranged and electrically connected in an electrical grid to facilitate drive control, equalization, and minimization of optical pathlength differences at particular wavelengths. In an embodiment, an optical filter is advantageously configured to provide intensity equalization across a specific LED subset. The substrate 370 is configured to provide a bulk temperature of the emitter array 400 so as to better determine LED operating wavelengths.

As shown in FIG. 5A, row drivers 376 and column drivers 378 are electrically connected to the light emitters 410 and activate one or more light emitters 410 by addressing at least one row 420 and at least one column 440 of an electrical grid. In an embodiment, the light emitters 410 each include a first contact 412 and a second contact 414. The first contact 412 of a first subset 430 of light emitters is in communication with a first conductor 420 of the electrical grid. The second contact 414 of a second subset 450 of light emitters is in communication with a second conductor 440. In an embodiment, each subset comprises at least two light emitters, and at least one of the light emitters of the first and second subsets 430, 450 are not in common. A detector 334 is capable of detecting the emitted light 402 and outputting a sensor signal responsive to the emitted light 402 after attenuation by the tissue site 1 via monitor connector 352. As such, the sensor signal is indicative of at least one physiological parameter corresponding to the tissue site 1, as described above.

FIG. 5B illustrates an emitter array 400 having LEDs 490 connected within an electrical grid of n rows and m columns totaling n+m drive lines 488, 486, where n and m integers greater than one. The electrical grid advantageously minimizes the number of drive lines required to activate the LEDs 490 while preserving flexibility to selectively activate individual LEDs 490 in any sequence and multiple LEDs 490 simultaneously. The electrical grid also facilitates setting LED currents so as to control intensity at each wavelength, determining operating wavelengths and monitoring total grid current so as to limit power dissipation. The emitter array 400 is also physically configured in rows 480. This physical organization facilitates clustering LEDs 490 according to wavelength so as to minimize pathlength variations and facilitates equalization of LED intensities.

As shown in FIG. 5B, one embodiment of an emitter array 400 comprises up to sixteen LEDs 490 configured in an electrical grid of four rows 480 and four columns 482. Each of the four row drive lines 488 provide a common anode connection to four LEDs 490, and each of the four column drive lines 486 provide a common cathode connection to four LEDs 490. Thus, the sixteen LEDs 490 are advantageously driven with only eight wires, including the four anode drive lines and the four cathode drive lines as shown. This compares favorably to conventional common anode or cathode LED configurations, which require more drive lines. In a particular embodiment, the emitter array 400 is partially populated with eight LEDs having nominal wavelengths as shown in TABLE 1. Further, LEDs having wavelengths in the range of 610-630 nm are grouped together in the same row. The emitter array 400 is adapted to a physiological measurement system 300 (FIG. 3A) for measuring $H_bCO$ and/or METHb in addition to $S_pO_2$ and pulse rate.

TABLE 1

| LED | λ | Row | Col |
|-----|-----|-----|-----|
| D1 | 630 | 1 | 1 |
| D2 | 620 | 1 | 2 |
| D3 | 610 | 1 | 3 |
| D4 |  | 1 | 4 |
| D5 | 700 | 2 | 1 |
| D6 | 730 | 2 | 2 |
| D7 | 660 | 2 | 3 |
| D8 | 805 | 2 | 4 |
| D9 |  | 3 | 1 |
| D10 |  | 3 | 2 |
| D11 |  | 3 | 3 |
| D12 | 905 | 3 | 4 |
| D13 |  | 4 | 1 |
| D14 |  | 4 | 2 |
| D15 |  | 4 | 3 |
| D16 |  | 4 | 4 |

Also shown in FIG. 5B, row drivers 376 and column drivers 484 located in the monitor 302 selectively activate the LEDs 490. In particular, row and column drivers 376, 484 function together as switches to Vcc and current sinks, respectively, to activate LEDs and as switches to ground and Vcc, respectively, to deactivate LEDs. This push-pull drive configuration advantageously prevents parasitic current flow in deactivated LEDs. In a particular embodiment, only one row drive line 488 is switched to Vcc at a time. One to four column drive lines 486, however, can be simultaneously switched to a current sink so as to simultaneously activate multiple LEDs within a particular row. LED drivers and the process of facilitating intensity equalization through the activation of two or more LEDs of the same wavelength are further described in the above-referenced app. Ser. No. 11/367,013, filed Mar. 1, 2006, entitled "Multiple Wavelength Sensor Emitters."

Although an emitter assembly is described above with respect to an array of light emitters each configured to transmit optical radiation centered around a nominal wavelength, in another embodiment, an emitter assembly advantageously utilizes one or more tunable broadband light sources, including the use of filters to select the wavelength, so as to minimize wavelength-dependent pathlength differences from emitter to detector. In yet another emitter assembly embodiment, optical radiation from multiple emitters each configured to transmit optical radiation centered around a nominal wavelength is funneled to a tissue site point so as to minimize wavelength-dependent pathlength differences. This funneling may be accomplished with fiberoptics or mirrors, for example. In further embodiments, the LEDs 490 can be configured with alternative orientations with correspondingly different drivers among various other configurations of LEDs, drivers and interconnecting conductors.

Automatic Wavelength Adjustment Processes

Figure 6A:
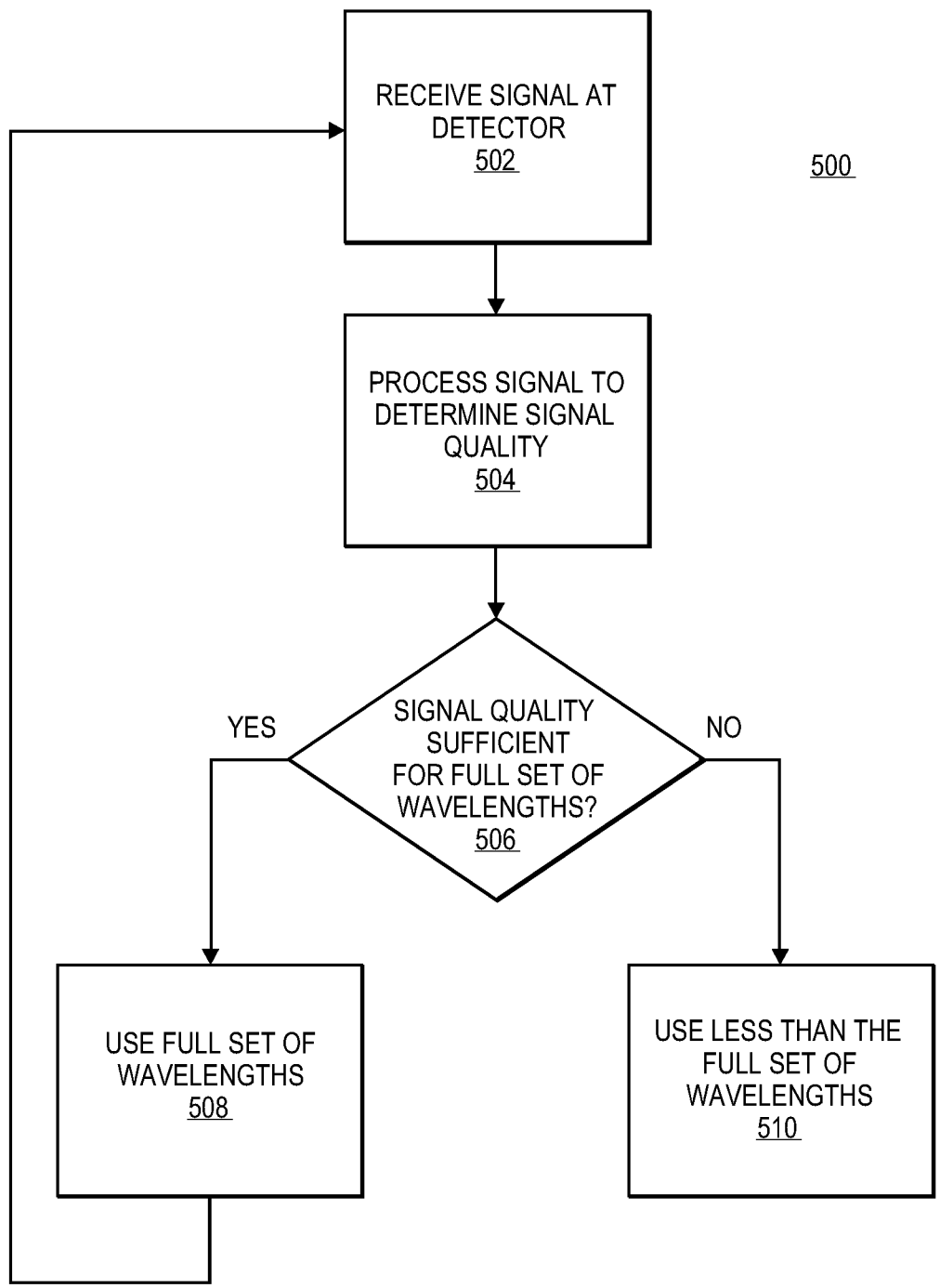
FIGS. 6A-6C are flow diagrams illustrating automatic wavelength adjustment processes in accordance with various embodiments.
Figure 6B:
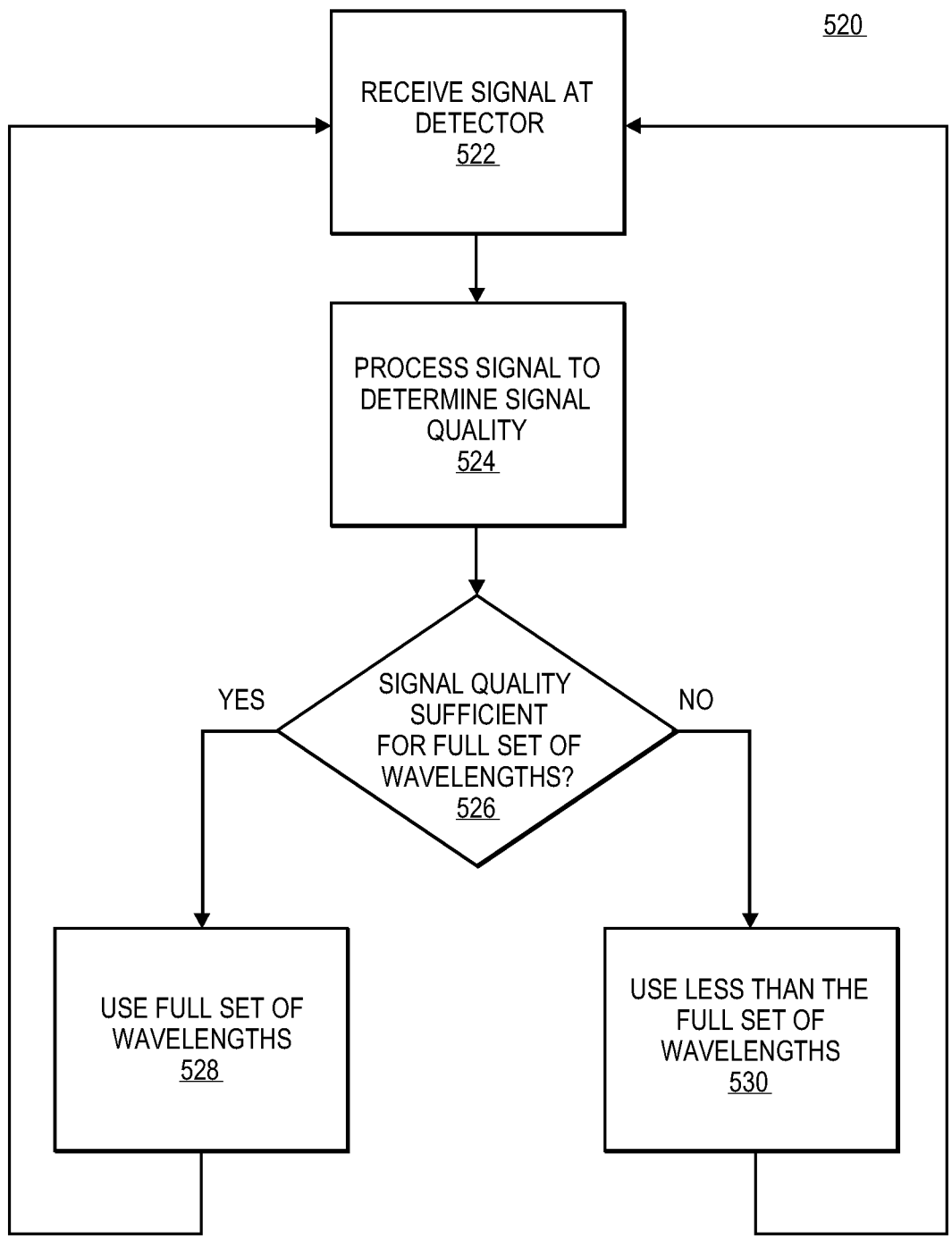
Figure 6C:
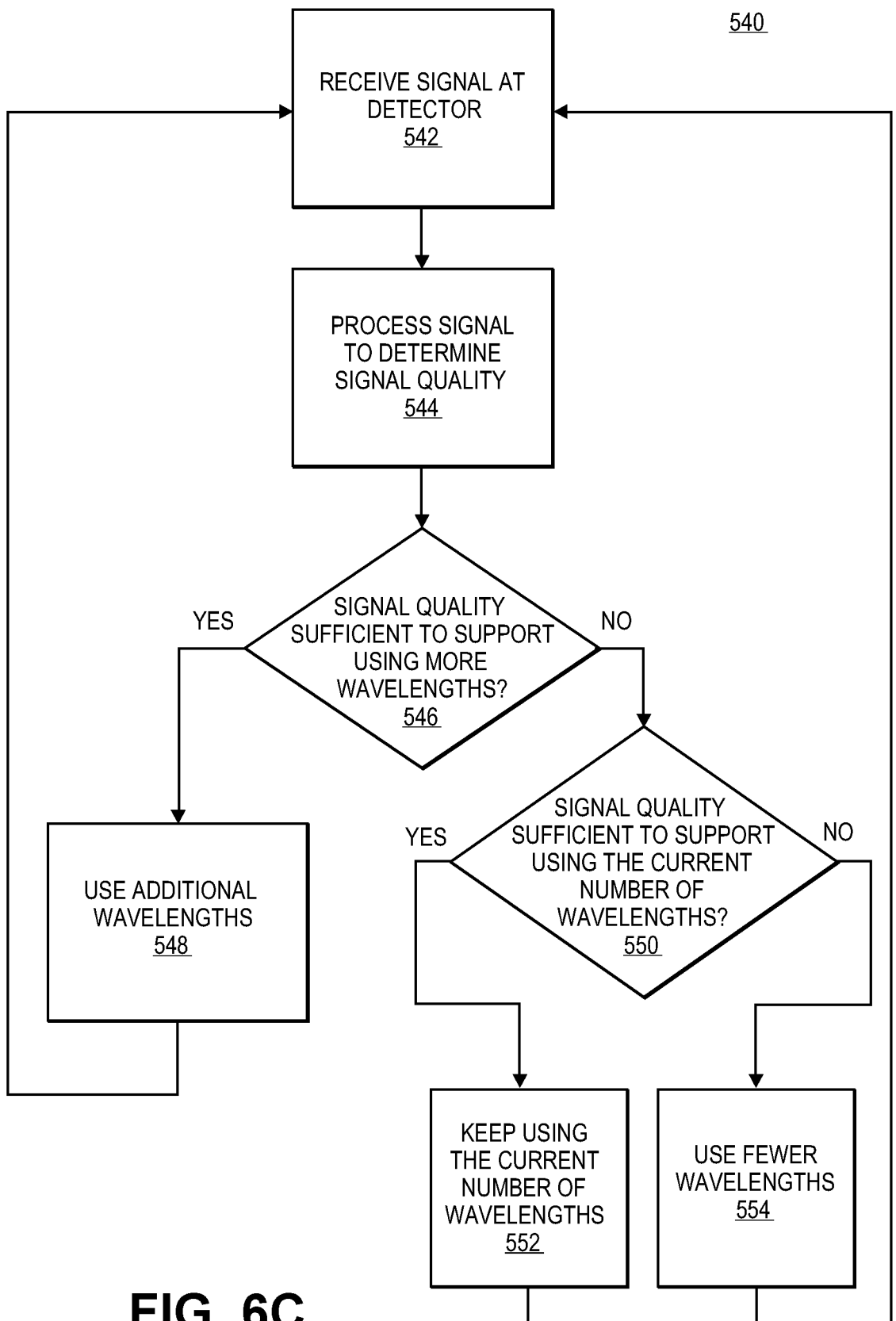

FIGS. 6A-6C are flow diagrams that illustrate the automatic wavelength adjustment processes in accordance with various embodiments. FIG. 6A illustrates an automatic wavelength adjustment process 500. In an embodiment, the process 500 is executed as part of or during a calibration process that is executed when the physiological measurement system 300 is first powered up and/or when the sensor assembly 310 is attached or re-attached to a tissue site. In another embodiment, the process 500 is executed periodically when the physiological measurement system 300 is in use.

As shown, the process 500 begins in an embodiment at block 502 with the detector 334 receiving a signal after tissue attenuation as described with respect to FIG. 4A. At block 504, the received signal is processed to determine signal quality. In an embodiment, the DSP 346 is configured to process the received signal that has been digitalized by the front-end 348 to determine signal quality. At block 506, the signal quality is evaluated to determine if it is sufficient to support a full set of active wavelengths. In an embodiment, the full set of active wavelengths includes the eight wavelengths as set forth in TABLE 1 above.

If the signal quality is determined to be lower than that which is needed to support the full set of active wavelengths, at block 510 the physiological measurement system 300 will use less than the full set of active wavelengths. In an embodiment, the DSP 346 sends a signal to the sensor controller 340 (FIG. 4B) to effectuate the use of less than the full set of active wavelengths. In an embodiment, the two active wavelengths used are at 660 nm (Red) and 905 nm (IR), the minimum two needed to detect SpO2. With reference to TABLE 1 and FIG. 5B, for example, LEDs D7 and D12 would be activated at block 510 while the rest of LEDs remain inactive.

In the alternative, if the signal quality is deemed to be sufficient to support the full set of active wavelengths, then at block 508 the physiological measurement system 300 will use the full set of active wavelengths. In an embodiment, the full set of active wavelengths includes the eight shown in TABLE 1. For example, the corresponding LEDs shown in TABLE 1 would be activated at block 508. In an embodiment, the process 500 then begins again at block 502. Various methods of determining and evaluating signal quality, including criteria for determining sufficiency of a signal quality to support a full set of active wavelengths, will be further described with respect to FIGS. 8A-12.

FIG. 6B shows another process 520 for automatic wavelength adjustment in which the physiological measurement system 300 periodically determines whether the full set of wavelengths should be used. The process 520 begins in an embodiment at block 522 with the detector 334 receiving a signal after tissue attenuation as described with respect to FIG. 4A. At block 524, the received signal is processed to determine signal quality. In an embodiment, the DSP 346 is configured to process the received signal that has been digitalized by the front-end 348 to determine signal quality. At block 526, the signal quality is evaluated to determine whether it is sufficient to support a full set of active wavelengths. In an embodiment, the full set of active wavelengths includes the eight wavelengths as set forth in TABLE 1 above.

If the signal quality is deemed to be lower than that which is needed to support the full set of active wavelengths, then at block 530 the physiological measurement system 300 will use less than the full set of active wavelengths. The DSP 346 can send a change signal to the sensor controller 340 (FIG. 4B) if the physiological measurement system 300 is currently using the full set of active wavelengths. For example, the change may reduce the number of active wavelengths from the eight shown in TABLE 1 to two (e.g., 660 nm (Red) and 905 nm (IR)). However, if the physiological measurement system 300 is already using less than the full set of active wavelengths, no action is performed at block 530. In either case, the process 520 returns to block 522 where a new signal will be received and processed at the next sampling cycle.

In the alternative, if the signal quality is deemed to be sufficient to support the full set of active wavelengths, then at block 528 the physiological measurement system 300 will either continue using the full set of active wavelengths (if the full set is already used) or change to using the full set of active wavelengths (if less than the full set is being used). If a change is needed, in an embodiment the DSP 346 can send a change signal to the sensor controller 340. The process 520 then returns to block 522, where a new signal will be received and processed at the next sampling cycle.

FIG. 6C shows another process 540 for automatic wavelength adjustment in which the physiological measurement system 300 periodically adjusts the number of wavelengths used depending on the detected signal quality. The process 540 begins in an embodiment at block 542 with the detector 334 receiving a signal after tissue attenuation as described with respect to FIG. 4A. At block 544, the received signal is processed to determine signal quality. In an embodiment, the DSP 346 is configured to process the received signal that has been digitalized by the front-end 348 to determine signal quality. At block 546, the signal quality is evaluated to determine whether it is sufficient to support additional active wavelengths. If so, then at block 548 the physiological measurement system 300 will use additional active wavelengths (if less than the full set is being used). If a change is needed, in an embodiment the DSP 346 can send a change signal to the sensor controller 340. The process 540 then returns to block 542, where a new signal will be received and processed at the next sampling cycle.

If the signal quality is deemed to not be sufficient to support more active wavelengths than those that are currently being used, then at block 550 the physiological measurement system 300 will determine whether the signal qualify can at least support the current set of active wavelengths. If it is sufficient, no action is taken at block 552 and the current number of active wavelengths will continue to be used. Otherwise, the physiological measurement system 300 will use fewer wavelengths. The DSP 346 can send a change signal to the sensor controller 340 (FIG. 4B). In any case, the process 540 returns to block 542 where a new signal will be received and processed at the next sampling cycle.

In various embodiments, portions of processes described in FIGS. 6A-6C can be performed at the front-end 348, the sensor controller 340, the DSP 346 or any other component within physiological measurement system 300.

Signal Quality Determination

Figure 7A:
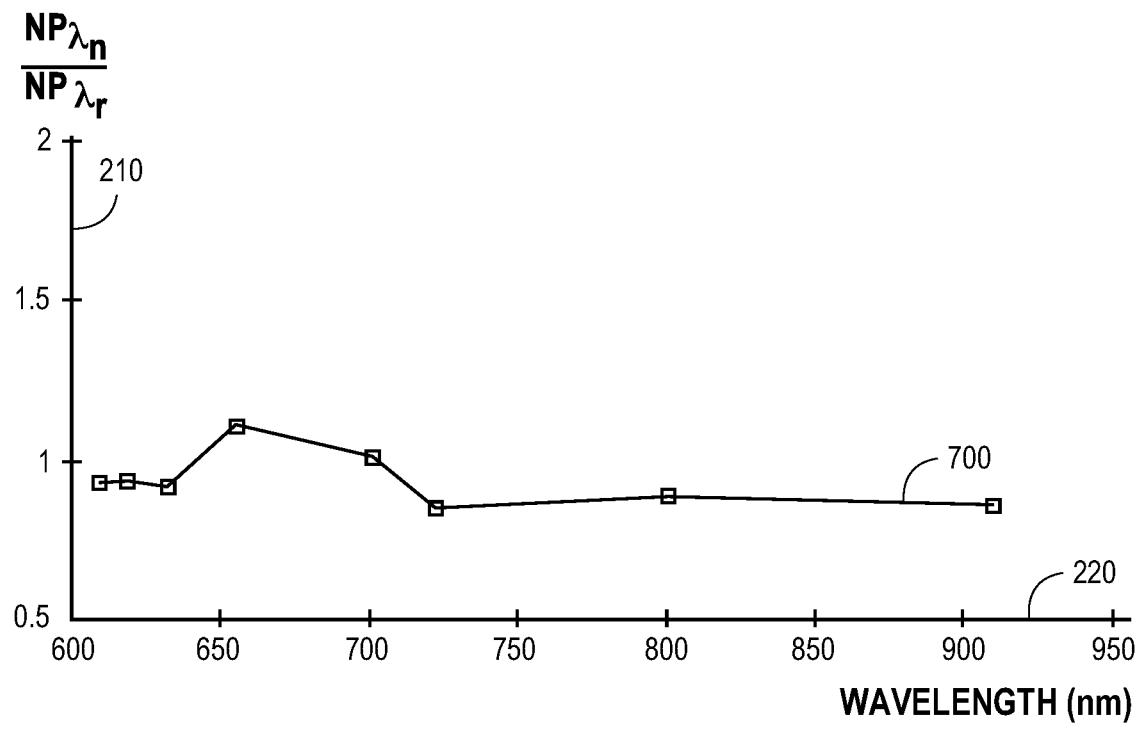
FIG. 7A is a graph of NP ratios versus wavelength illustrating a probe-off profile.
Figure 7B:
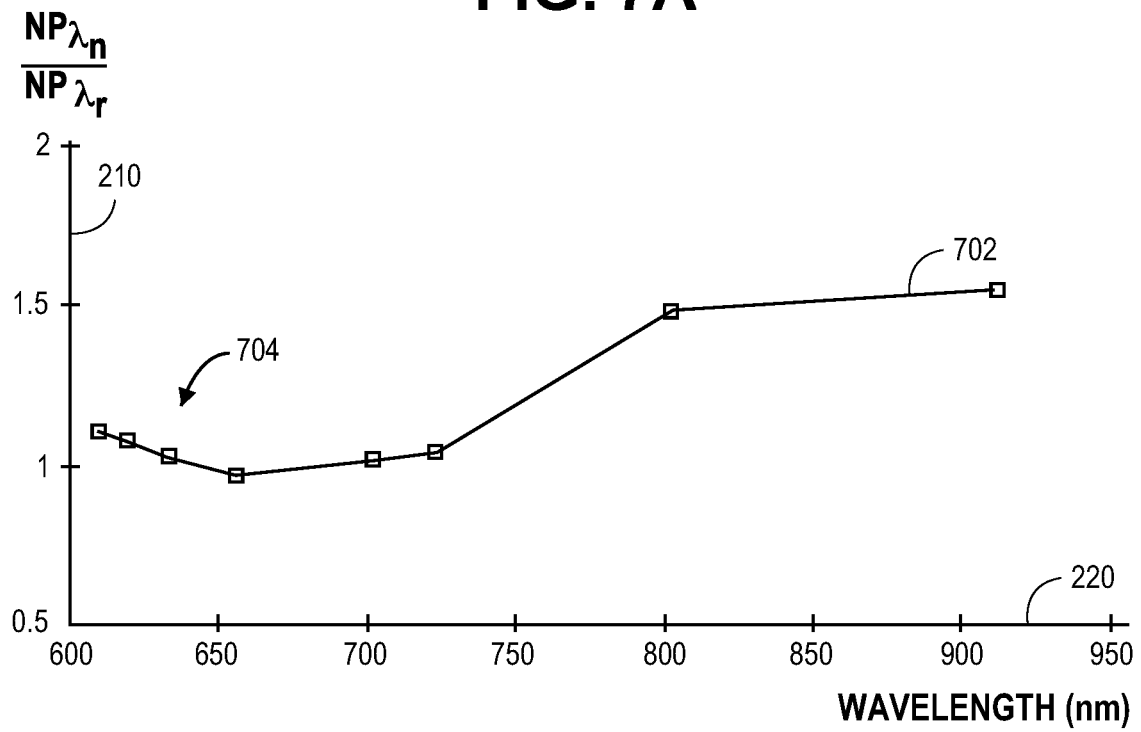
FIG. 7B is a graph of NP ratios versus wavelength illustrating a penumbra profile.

FIGS. 7A-7B illustrate profiles of two conditions that are indicative of degraded signal quality. FIGS. 8A-11B describe example methods of deriving a confidence measurement that can be used to measure signal quality, and in particular, to detect degraded signal quality shown in the examples illustrated below.

FIG. 7A illustrates an example of a probe-off profile 700. When a sensor is completely dislodged from a patient, a so-called "probe off" condition occurs. Despite a probe off condition, an optical sensor may continue to detect an AC signal, which can be induced at the detector by other than pulsatile arterial absorption of LED emitted light. For example, small patient movements, vibrations, air flow or other perturbations may cause the pathlength between the LEDs and the detector to vary, resulting in an AC detector signal that can be mistakenly interpreted by the monitor as due to pulsatile arterial blood. Further, ambient light may reach the detector, and any modulation of the ambient light due to AC power, power fluctuations, moving objects, such as a fan, among other perturbations can be also mistaken as a pulsatile arterial signal. Probe off errors are serious because a blood constituent monitor may display normal results, such as oxygen saturation, when, in fact, the sensor is not properly attached to the patient, potentially leading to missed severe desaturation events. As shown in FIG. 7A, a probe-off profile 700 is readily apparent as it does not have a shape related to the absorption characteristics of hemoglobin constituents.

FIG. 7B illustrates an example of a penumbra profile 702. When a sensor is not properly positioned or becomes partially dislodged, a penumbra condition may occur, where the detector is "shadowed" by a tissue site, such as a finger, but also receives some light directly from the emitters or indirectly reflected off the sensor housing, or both. As a result, the DC signal at the detector rises significantly, which lowers the AC/DC ratio (NP). Because red wavelengths are more significantly absorbed by Hb and HbO2, the penumbra condition is most noticeable at the red portion 704 of the $NP_{\lambda_i}/NP_{\lambda_r}$. This effect is readily seen in the penumbra profile 702 as compared to a normal tissue profile 200 (FIG. 2).

Advantageously, a physiological parameter confidence measurement system, as described below, can distinguish a tissue profile 200 (FIG. 2) from a probe-off profile 700 (FIG. 7A) or penumbra profile 702 (FIG. 7B), as examples. Further, a physiological parameter confidence measurement system can provide indications that the detector signal is degraded as the result of various physiological and non-physiological phenomenons.

Physiological Parameter Confidence Measurement System

Figure 8:
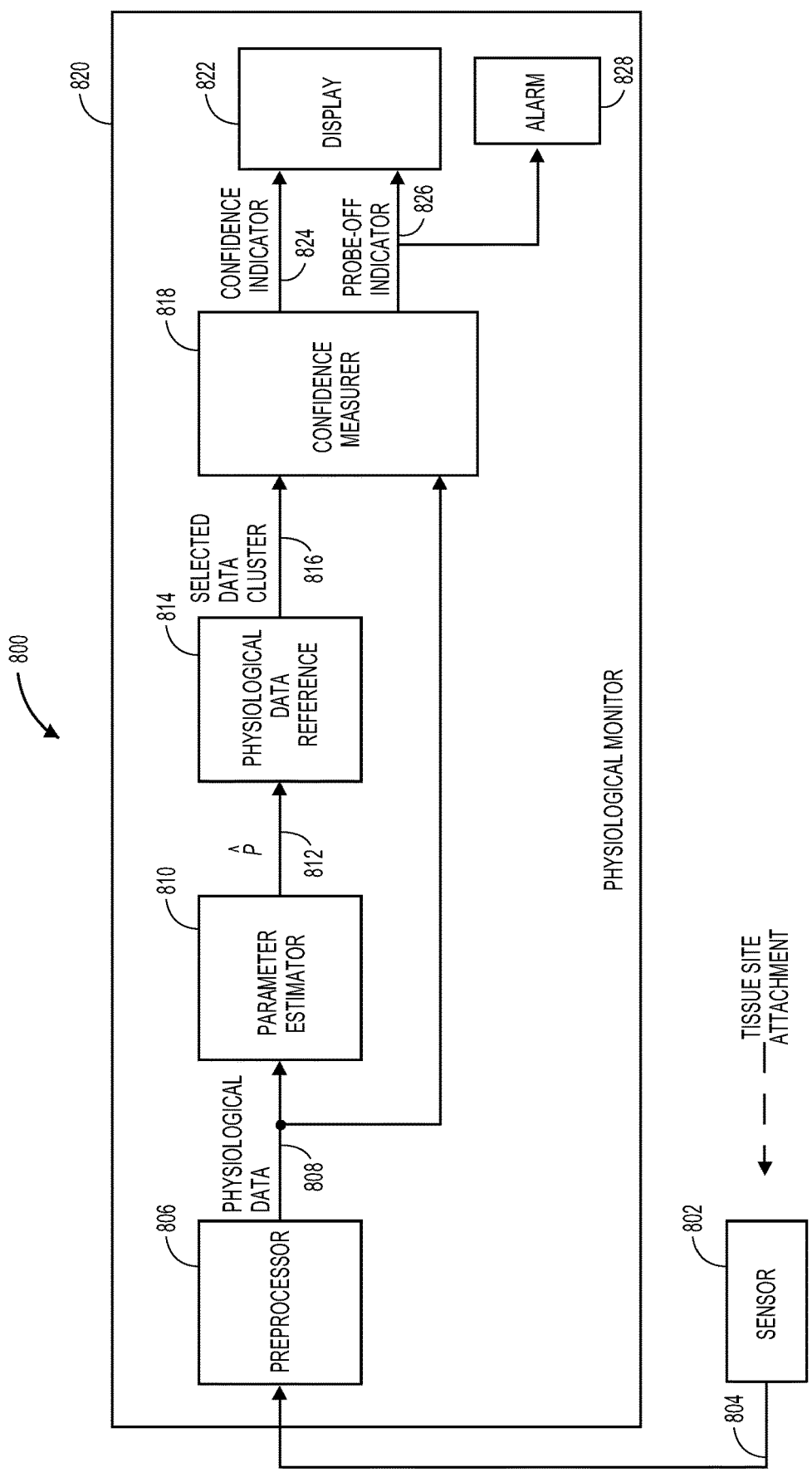
FIG. 8 is a general block diagram of a confidence measurement system.

FIG. 8 illustrates a physiological parameter confidence measurement system 800 having a physiological data 808 input, a confidence indicator 824 output and a probe-off indicator 826 output. In an embodiment, physiological data 808, such as the NP ratios described above, is derived from a sensor 802 generating a sensor signal 804 responsive to multiple wavelengths of optical radiation transmitted into and attenuated by a tissue site. The confidence indicator 824 provides an observer with some measure of "goodness" for the physiological data 808. That is, if confidence is high, it is likely the physiological data 816 is representative of a physiological condition or state. If confidence is low, the physiological data 808 may be less representative of a physiological condition or state. If the confidence is very low, a probe-off indicator 826 may be generated to alert an observer to the possibility that a sensor from which the physiological data 808 is derived is not properly positioned on a tissue site and may not be generating physiologically significant data. In an embodiment, a confidence measure may be provided as a percentage, such as 0-100%.

The confidence measure can be used to measure signal quality in the processes described above with respect to FIGS. 6A-6C. For example, the confidence level threshold may be set at 80% in order for a full set of wavelengths to be used. In other embodiments, the threshold may be set by the user of the physiological measurement system 300. In various embodiments, a confidence indicator 824 corresponding to a confidence measure may be visual (through a display 822) or audible (through an alarm 828) or both. The visual or audible indication may assist the user in setting the threshold.

As shown in FIG. 8, the physiological parameter confidence measurement system 800 also has a parameter estimator 810, a physiological data reference 814 and a confidence measurer 818. The parameter estimator 810 derives one or more physiological parameter estimates, P̂, 812 based upon the physiological data 810. The parameter estimate or estimates 812 are used to select one or more data clusters 816 from the physiological data reference 814. In an embodiment, the physiological data reference 814 is a collection of predetermined physiological data organized in data clusters. For example the physiological data reference 814 may contain clinically-derived physiological data organized according to corresponding values of a physiological parameter determined by a "gold standard" instrument. In a particular embodiment, the physiological data are NP ratios obtained for various physiological parameters, such as SpO₂, HbCO, HbMet, Hbt, fractional oxygen saturation, bilirubin or glucose to name a few, as measured with a standardized cooximeter, for example. In an embodiment, the physiological data reference 814 is a non-volatile memory or other data storage device containing predetermined physiological data. The confidence measurer 818 uses the physiological data 808 and the selected data cluster or data clusters 816 to generate the confidence indicator 824, the probe-off indicator 826 or both.

A confidence measurement and confidence indicator, as described herein, may be combined with other signal quality and data confidence measurements and indicators, such as those described in U.S. Pat. No. 6,996,427 titled Pulse Oximetry Data Confidence Indicator and U.S. Pat. No. 6,606,511 titled Pulse Oximetry Pulse Indicator, both patents assigned to Masimo Corporation, Irvine, Calif. and incorporated by reference herein. A probe off measurement and probe off indicator as described herein may be combined with other probe off measurements and indicators, such as those described in U.S. Pat. No. 6,654,624 titled Pulse Oximeter Probe-Off Detector and U.S. Pat. No. 6,771,994 titled Pulse Oximeter Probe-Off Detection System, both patents assigned to Masimo Corporation, Irvine, Calif. and incorporated by reference herein.

Figure 9A:
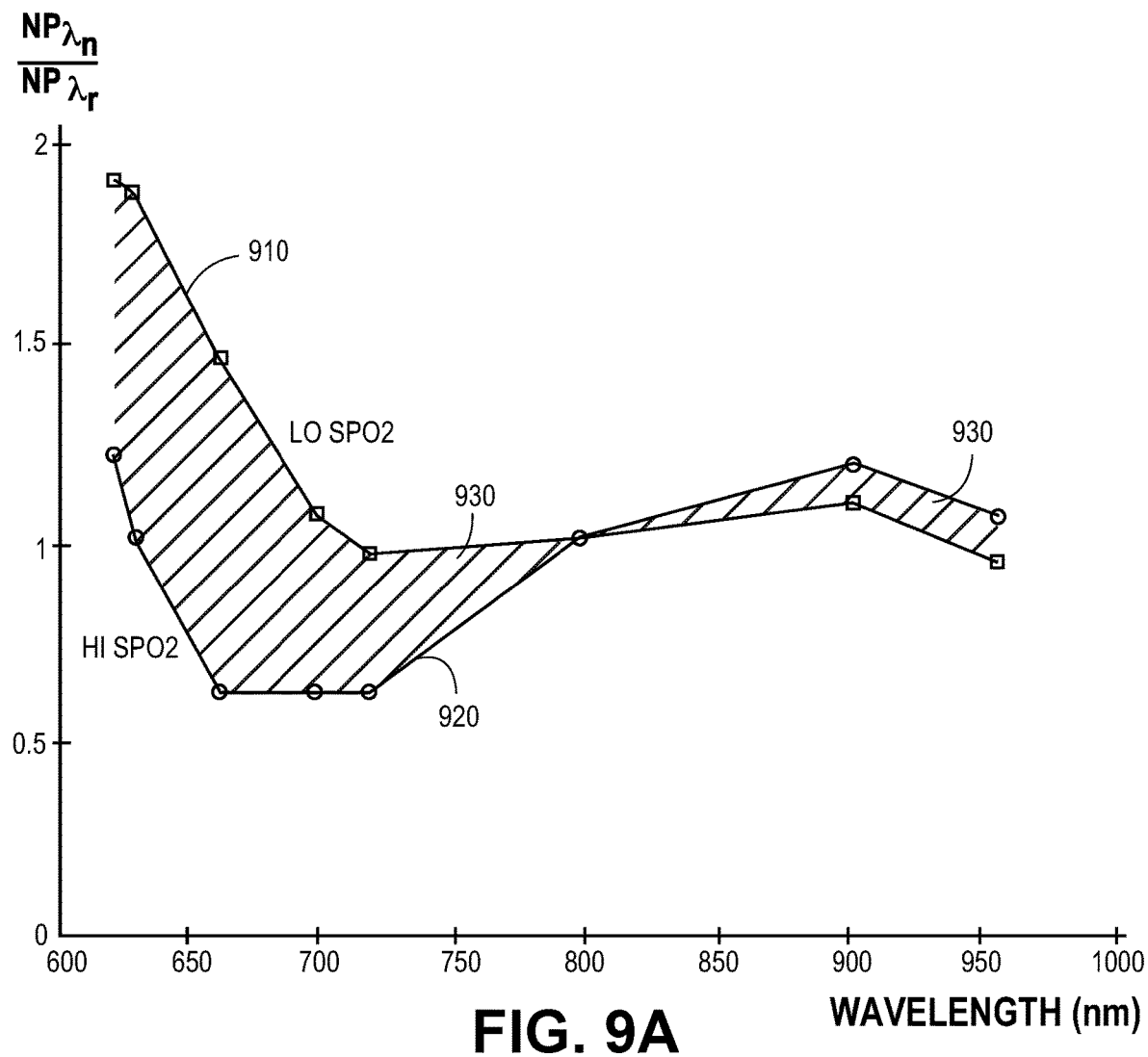
FIG. 9A is a graph of normalized plethysmograph (NP) ratios versus wavelength for low and high $SpO_2$ illustrating a NP envelope.

FIG. 9A illustrates NP ratio versus wavelength curves computed from a multiple wavelength sensor, such as described in the U.S. patent application titled "Multiple Wavelength Sensor," referenced above. In this example, the sensor emits eight wavelengths (620, 630, 660, 700, 730, 805, 905 and 960 nm). As with FIGS. 8A and 8B, the confidence measurement derived from the embodiments shown in FIGS. 9A and 9B can be used to adjust the number of active wavelengths that is used by the physiological measurement system 300.

Shown in FIG. 9A is a low oxygen saturation curve 610, e.g. SpO₂=70% and a high oxygen saturation curve 620, e.g. SpO₂≈100%. By comparison, a conventional two wavelength pulse oximetry sensor, as described above, results in a single point on a particular curve. Advantageously, the NP ratio curves 910, 920 represent a tissue profile that can be compared to a particular sensor response to determine if a physiologically significant measurement has been made. In an embodiment, the NP ratio curves 910, 920 delineate the boundaries of a physiologically significant NP ratio region 930. Although described above with respect to SpO₂, such regions or boundaries can be derived for other physiological parameters such as HbCO, HbMet, Hbt, fractional oxygen saturation, bilirubin or glucose to name a few.

Figure 9B:
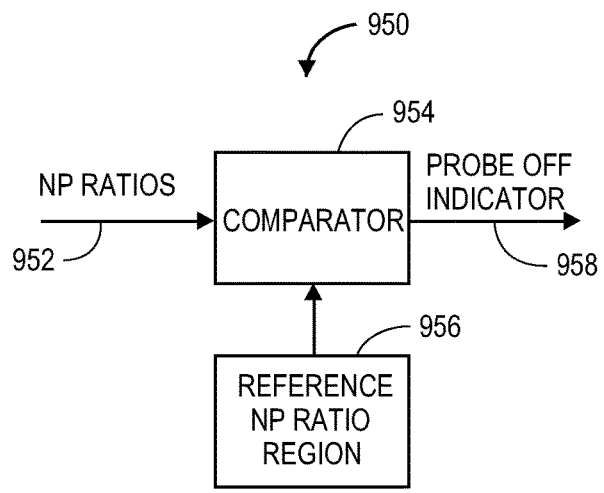
FIG. 9B is a block diagram of a multiple wavelength probe off detector utilizing an NP envelope.

FIG. 9B illustrates one embodiment of a physiological parameter confidence measurement system 950 utilizing a NP ratio region such as described with respect to FIG. 9A, above. The confidence measurement system 950 has input NP ratios 952 measured in response to a multiple wavelength sensor, reference NP ratio region 956 that delineates physiologically significant NP ratios 930 (FIG. 9A), and a comparator 954. In one particular embodiment, the NP ratio region 956 is predetermined from clinically-derived data for one or more parameters of interest, such as SpO₂, HbCO, HbMet, Hbt, fractional oxygen saturation, bilirubin or glucose, to name a few. In another particular embodiment, the NP ratio region 956 is theoretically calculated. The comparator 954 compares the input NP ratios 952 with the NP ratio region 956 and generates a probe-off indicator 958 if any, or more than a predetermine number, of the input NP ratios 952 fall outside of an NP ratio region 956.

Figure 10A:
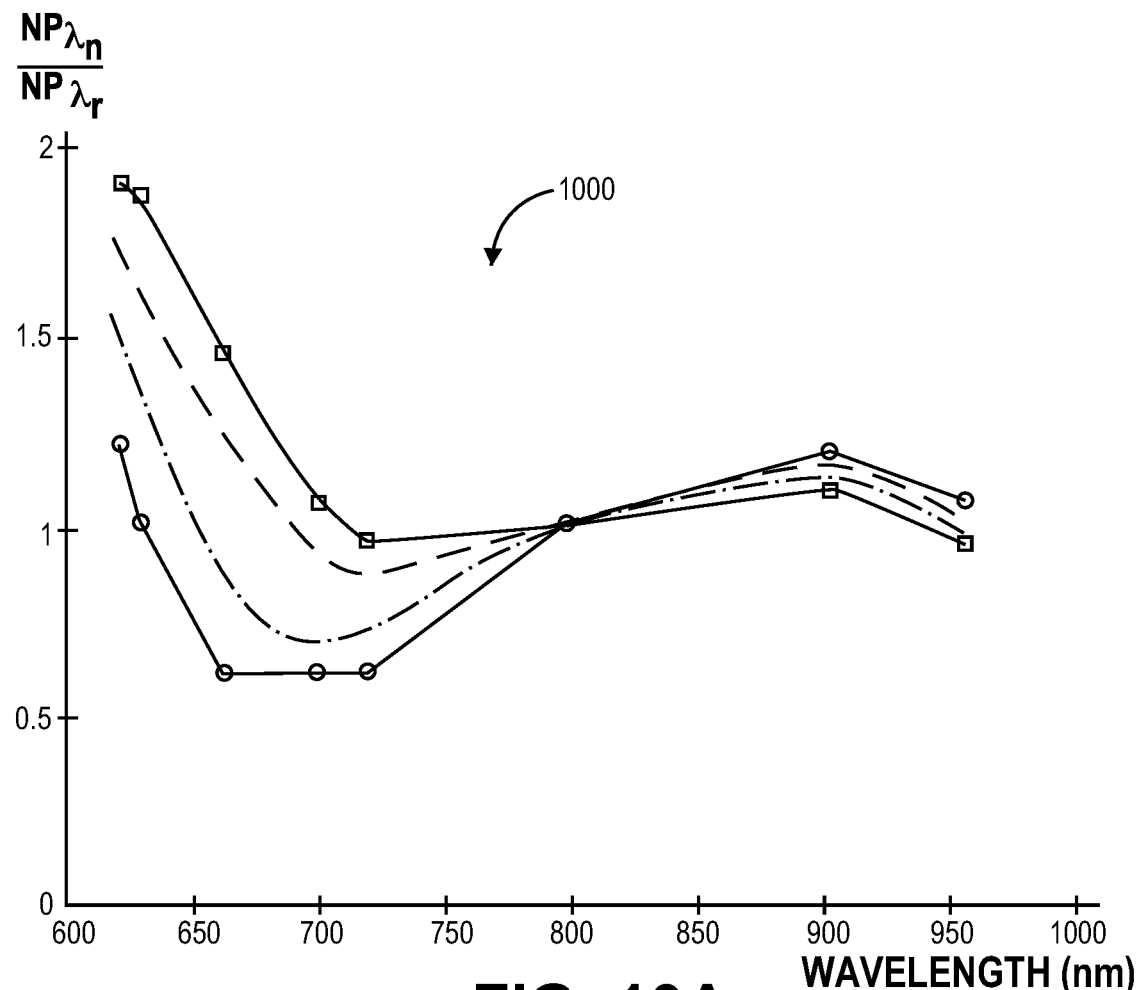
FIG. 10A is a graph of NP ratios versus wavelength illustrating a family of parametric NP curves.

FIG. 10A illustrates a family of parametric NP ratio versus wavelength curves 1000 computed from a multiple wavelength sensor, such as referenced above. Each curve represents a different value of a measured parameter, such as $SpO_2$. For example, there may be a curve for each of $SpO_2$=70%, 75%, 80%, . . . 100%. Advantageously, such curves more precisely indicate physiologically significant multiple wavelength sensor measurements as compared to a bounded NP ratio region 930 (FIG. 9A) such as described with respect to FIGS. 9A-9B, above. The confidence measurement derived by the method shown in FIGS. 10A-10B can be used to adjust the number of active wavelengths that is used by the physiological measurement system 300.

Figure 10B:
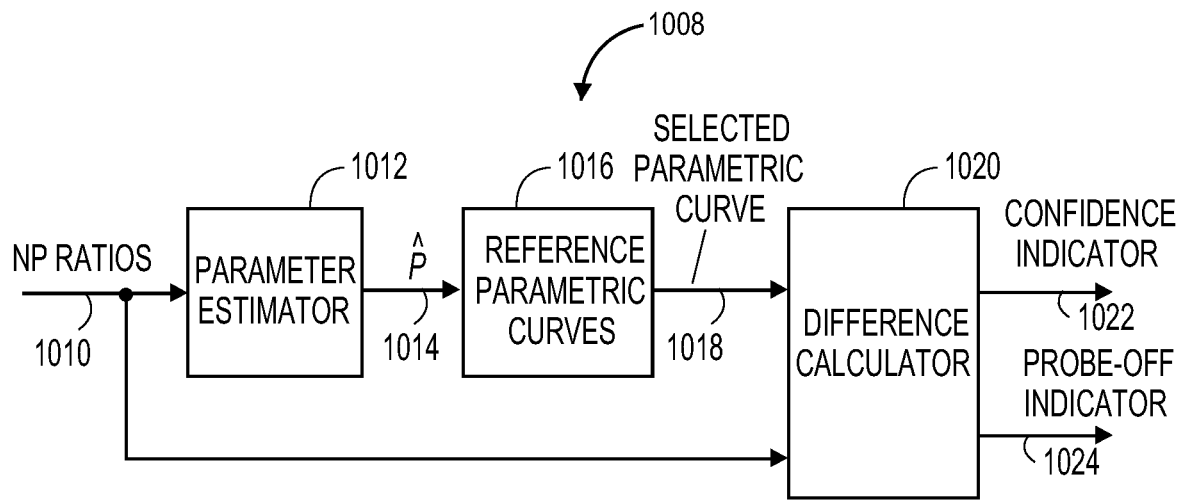
FIG. 10B is a block diagram of a multiple wavelength confidence measurement system utilizing parametric NP curves.

FIG. 10B illustrates another embodiment of a physiological parameter confidence measurement system 1008 utilizing parametric NP ratio curves, such as described with respect to FIG. 10A, above. The confidence measurement system 1008 has input NP ratios 1010 measured in response to a multiple wavelength sensor, a parameter estimator 1012, reference parametric curves 1016 and a difference calculator 1020. The parameter estimator 1012 inputs the NP ratios 1010 so as to generate a parameter estimate 1014, such as $SpO_2$, HbCO, HbMet, Hbt, fractional oxygen saturation, bilirubin or glucose, to name a few. The estimated parameter 1014 selects one or more of the reference parametric curves 1016, which are predetermined from clinically-derived data that is stored in memory or data that is mathematically pre-calculated or calculated in real time and stored in memory. The difference calculator 1020 measures the difference between the NP ratios 1010 and the selected parametric curve 1016. For example, a mean-squared error calculation can be made between the input NP ratios 1010 and the selected parametric curve 1018. The resulting difference calculation is used as a confidence measure or translated into a confidence measure and a confidence indicator output 1022 is generated accordingly. Alternatively, or in addition to a confidence measure, a probe off condition can be indicated if the difference calculation is larger than a predetermined value or the confidence measure is less than a predetermined value. In another embodiment, a correlation calculator is used in place of the difference calculation. The confidence measurement derived from the embodiments shown in FIGS. 10A-10B can also be used to adjust the number of active wavelengths that is used by the physiological measurement system 300.

Figure 11A:
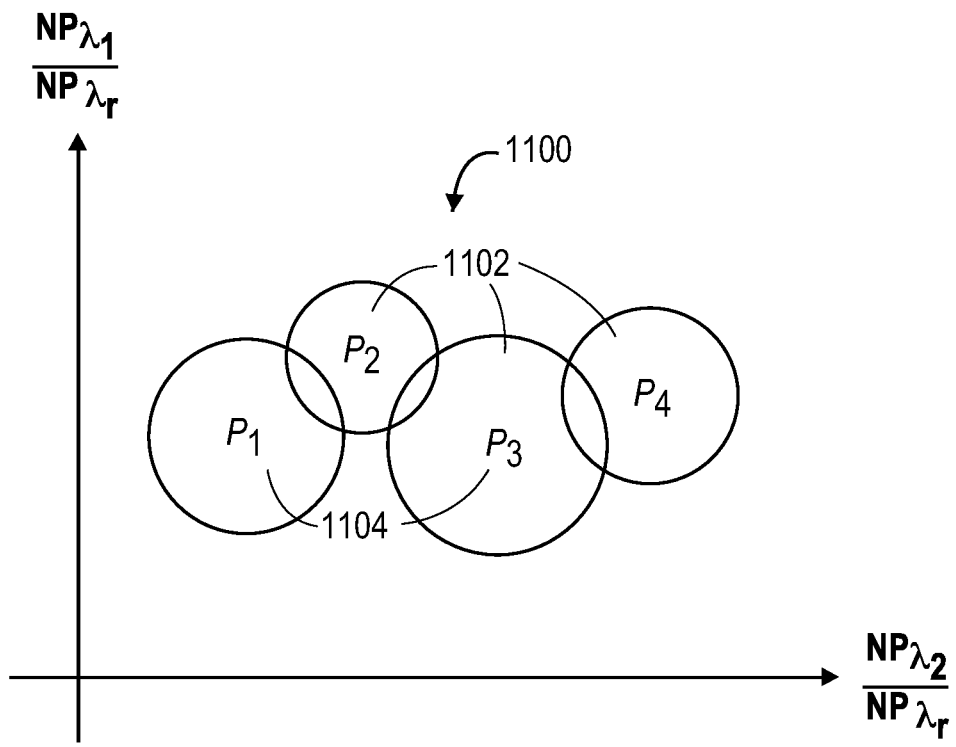
FIG. 11A is an NP ratio graph illustrating a family of NP data clusters.

FIG. 11A illustrates a family of data clusters 1100 shown in two dimensions by way of example. Each data cluster 1100 represents NP ratios clinically measured across a population for specific values 1104 of a selected parameter P, such as $P_1$, $P_2$, $P_3$ and $P_4$ as shown. Each data cluster 1100 defines a region 1102 of NP ratios measured for a particular parameter value 1104 and has a probability distribution, such as a normal distribution, over the indicated region 1102.

For example, the clinical data can be organized as a table of known values of P, corresponding NP ratios measured over a population, and the relative number of occurrences of particular NP ratio values for each value of P. The relative number of occurrences of particular NP ratio values for a particular value of P yields an NP ratio probability distribution for that value of P. Thus, each P value 1104 in the table has a corresponding data cluster 1100 of measured NP ratios and an associated probability distribution for those NP ratios.

Figure 11B:
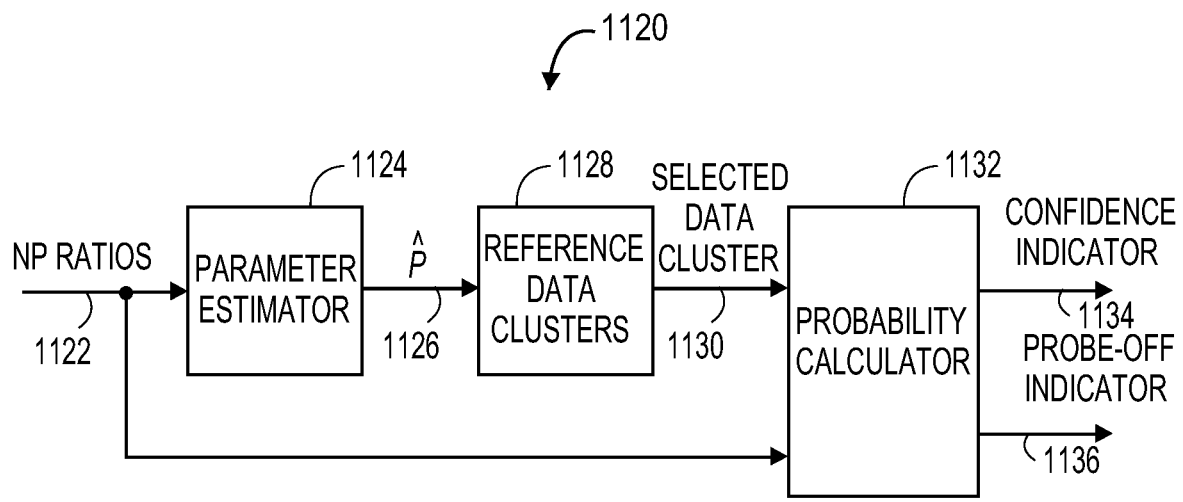
FIG. 11B is a block diagram of a multiple wavelength confidence measurement system utilizing NP data clusters.

FIG. 11B illustrates yet another embodiment of a physiological parameter confidence measurement system 1120 utilizing NP data clusters and corresponding probability distributions, such as described with respect to FIG. 11A, above. The confidence measurement system 1120 has input NP ratios 1122 measured in response to a multiple wavelength sensor, a parameter estimator 1124, reference data clusters 1128 and a probability calculator 1132. The parameter estimator 1124 inputs the NP ratios 1122 so as to generate a parameter estimate 1126, such as described with respect to other embodiments, above. In an embodiment, the reference data clusters 1128, such as described with respect to FIG. 11A, are stored in a memory device, such as an EPROM. The estimated parameter 1130 is compared with the reference data clusters 1140 so as to determine the closest region 1102 (FIG. 11A) or closest overlapping portion of two regions 1102 (FIG. 11A). The probability calculator 1132 computes a probability based upon the distribution above the selected region 1102 (FIG. 11A). A confidence measure is also derived based upon the calculated probability. In a particular embodiment, the confidence measure is the calculated probability. A confidence indicator 1134 is generated in response to the confidence measure. In an embodiment, if the confidence probability or the calculated confidence measure is below a predetermined threshold, a probe-off indicator 1136 is generated. In particular embodiments, the confidence indicator 1134 or probe-off indicator 1136 or both may be alphanumeric or digital displays, optical indicators or alarms or similar audible indicators, to name a few. The confidence measurement derived from the embodiments shown in FIGS. 11A-11B can also be used to adjust the number of active wavelengths that is used by the physiological measurement system 300.

Automatic Wavelength Adjustment During Calibration

Besides utilizing the confidence measurements derived from the methods and systems shown in FIGS. 8A-11B for automatic wavelength adjustment, embodiments of the physiological measurement system 300 can also automatically adjust the number of active wavelengths based on the results of a calibration process.

Figure 12:
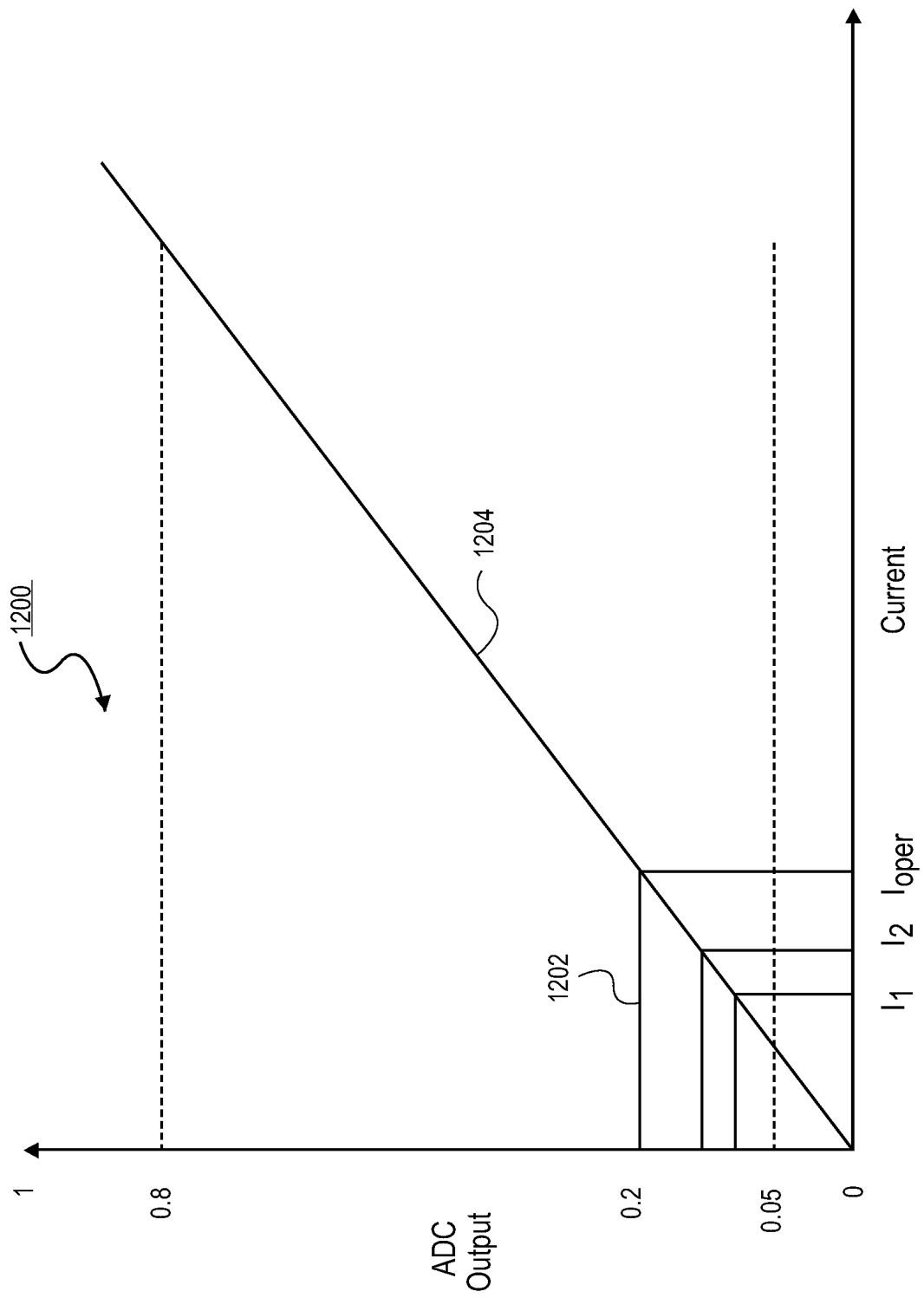
FIG. 12 is a graph showing a ratio of normalized detector signal to current provided to an LED.

FIG. 12 shows a graph 1200 illustrating a signal calibration process performed by the physiological measurement system 300. The graph plots the Analog-to-Digital Conversion (ADC) signal output (i.e. the digitalized sensor signal) against the current supplied to an LED in the emitter assembly 332. The ADC output may be from the front-end 348 shown in FIG. 4A, for example. As shown, the ADC signal output ranges from 0 to 1 on a normalized scale. In an embodiment, an ideal range of output is preferably between 0.05 to 0.80, with an ideal operational output at about 0.2. The ideal range of output provides a proper determination of physiological data measurements.

In an embodiment, the physiological measurement system 300 performs calibration by sending a small test current through each of the LEDs that is used in emitting optical radiation at the full set of active wavelengths (e.g. the LEDs shown in TABLE 1). The system can, for example, send a 5 milliamp current, as denoted by the symbol $I_1$ in graph 1200. The detector then records the detected signal after tissue attenuation. A sample input-output is shown in line 1204, which illustrates the ratio of measured, digitalized sensor signal to the input current provided to the LED. The calibration can then send an additional, larger test current through the LED, e.g. 10 milliamps, as denoted by the symbol $I_2$. Based on the level of the measured sensor signal(s) in response to the one or more test currents provided to the LED, the physiological measurement system 300 can determine whether a sensor signal output in the acceptable range can be obtained when a larger operational current is applied. For example, the physiological measurement system 300 can use the measured outputs from the test currents to extrapolate a likely sensor signal output 1202 (shown in FIG. 12 as having a normalized ADC of 0.2) based on an anticipated operational current $I_{oper}$. In an embodiment, the DSP 346 performs these determination calculations. In other embodiments, they are performed by other components such as the front end 348.

In an embodiment, the calibration performs the same or similar test for each of the LEDs that is used in emitting optical radiation at the full set of active wavelengths, and determines whether the extrapolated signal output for the LED(s) for each individual wavelength is acceptable. In the example configuration shown in TABLE 1, where there is a one-to-one correspondence between LEDs and wavelengths, the calibration process would determine whether the extrapolated signal output for each LED is within the acceptable range. In an embodiment, the extrapolation takes into account that while each active LED may be driven by a different amount of operational current, an overall gain is applied to all active LEDs in the emitter array. Therefore, in an embodiment, the calibration process also attempts to determine an operational current for each active LED in order to have all sensor signals fall within the acceptable ADC range, as illustrated in the example in FIG. 12.

In an embodiment, if one or more extrapolated signal outputs for a particular wavelength are not in the acceptable range, the physiological measurement system 300 uses a fewer number of active wavelengths, i.e., the associated LED(s), than the full set of active wavelengths. For example, in an embodiment where the full set of active wavelengths comprises eight wavelengths, if any of the eight wavelengths returns an unacceptable result in calibration, the reduction can go from eight active wavelengths to two. The two can be of the wavelengths 660 nm (red) and 905 nm (IR), the two needed for providing a SpO2 reading. In an embodiment, the LED(s) for the two active wavelengths are activated at a longer duty cycle (½ cycle/wavelength) than when the full set of active wavelengths is used (⅛ cycle/wavelength).

In other embodiments, the number of active wavelength is first reduced from eight to four, and then from four to two. In embodiments in which the physiological measurement system includes twelve active wavelengths, the number can be progressively reduced from twelve to eight to four to two, if the calibration results necessitate such a reduction. In other embodiments, the physiological measurement system 300 does not follow a pre-set reduction routine but instead attempts to maximize the number of physiological data measurements that can be obtained given the number of wavelengths that pass the calibration test. Thus, for example, instead of reducing from twelve to two when one wavelength fails the calibration test, the physiological measurement system 300 can reduce to ten, if the remaining ten can all be used to determine physiological data measurements.

Additional Embodiments

In an embodiment, the physiological measurement system 300 may return at least one physiological data measurement even when the detected signal does not support a full set of physiological data measurements. For example, if the detected signal indicates that a patient's perfusion is too low to support an Hb measurement but can otherwise support a SpO2 measurement, the physiological measurement system 300 may return the SpO2 measurement.

In an embodiment, the patient's perfusion level is used in the afore-mentioned confidence calculations. In an embodiment, the observed perfusion index is used as a factor in determining confidence. In another embodiment, the confidence level is determined based on perfusion alone. For example, an observed perfusion index that is outside of an acceptable range (e.g. below a threshold) would lead to a low confidence level.

In an embodiment, the physiological measurement system 300 provides user options for configuring the use of less than a full set of wavelengths. The options allow a user to configure the physiological measurement system 300 to specify the manner in which the number of wavelengths are reduced based on user-specified or pre-specified confidence level(s). For example, a user can configure the physiological measurement system 300 to use two wavelengths if the confidence level drops below a certain user-specified or pre-specified level. In another embodiment, a user can configure a confidence level below which a particular physiological data measurement is not returned by the physiological measurement system 300.

A multiple wavelength sensor with automatic wavelength adjustment has been disclosed in detail in connection with various embodiments. These embodiments are disclosed by way of examples only and are not to limit the scope of the claims that follow. One of ordinary skill in art will appreciate many variations and modifications.

What is claimed is:

1. An optical non-invasive physiological parameter measurement system comprising:
   one or more light emitting sources configured to emit light at a plurality of wavelengths;
   a sensor configured to detect light emitted by the one or more light emitting sources after the emitted light is attenuated by body tissue, and to generate an output signal useable to measure at least one physiological parameter of the body tissue; and
   a processor configured to:
   cause the one or more light emitting sources to emit light at a first set of the plurality of wavelengths;
   determine a physiological parameter estimate from a first output signal received from the sensor based on detected light emitted at the first set of the plurality of wavelengths;
   determine a physiological data reference based on the physiological parameter estimate;
   determine a confidence measurement value based on the first output signal and the physiological data reference;
   cause the one or more light emitting sources to emit light at a second set of the plurality of wavelengths by deactivating at least one of the plurality of wavelength emissions when the confidence measurement value is less than a threshold value; and
   determine a physiological parameter measurement based on a second output signal received from the sensor based on detected light emitted at the second set of the plurality of wavelengths.

2. The system of claim 1, wherein the processor is further configured to:
   determine a second physiological parameter estimate from the second output signal received from the sensor based on detected light emitted at the second set of the plurality of wavelengths;

determine a second confidence measurement value based on the second physiological parameter estimate and a second physiological data reference; and activate at least one of deactivated wavelength emissions when the confidence measurement value is greater than the threshold value.

3. The system of claim 1, wherein the physiological data reference comprises a normalized plethysmograph ratio region bounded by a high normalized plethysmograph ratio curve and a low normalized plethysmograph ratio curve.

4. The system of claim 3, wherein the high normalized plethysmograph ratio curve is a high oxygen saturation ($SpO_2$) curve and the low normalized plethysmograph ratio curve is a low oxygen saturation ($SpO_2$) curve.

5. The system of claim 1, wherein the physiological data reference comprises a reference parametric curve that is predetermined from clinically-derived data.

6. The system of claim 1, wherein the physiological data reference comprises a data cluster defining a region of normalized plethysmograph values.

7. The system of claim 1, wherein the second set of the plurality of wavelengths comprises two wavelengths.

8. The system of claim 7, wherein one of the two wavelengths is in the red range and the other of the two wavelengths is in the infrared range.

9. The system of claim 1, wherein the plurality of wavelengths comprises at least eight wavelengths.

10. The system of claim 1, wherein the physiological parameter measurement comprises a $SpO_2$, HbCO, HbMet, Hbt, factional oxygen saturation, bilirubin, or glucose measurement.

11. A method for automatically adjusting a number of a plurality of wavelengths used in a physiological measurement system, the method comprising:

emitting light at a first set of a plurality of wavelengths with one or more light emitting sources;

detecting, with a sensor, light emitted by one or more light emitting sources after attenuation by body tissue, the sensor generating a first output signal;

determining a physiological parameter estimate from the first output signal received from the sensor based on the detected light emitted at the plurality of wavelengths;

determining a physiological data reference based on the physiological parameter estimate;

determining a confidence measurement value based on the first output signal and the physiological data reference;

deactivating at least one of the plurality of wavelength emissions when the confidence measurement value is less than a threshold value to cause the plurality of light emitting sources to emit light at a second set of the plurality of wavelengths; and determining a physiological parameter measurement based on a second output signal received from the sensor based on the detected light emitted at the second set of the plurality of wavelengths.

12. The method of claim 11, further comprising:

determining a second physiological parameter estimate from the second output signal received from the sensor based on detected light emitted at the second set of the plurality of wavelengths;

determining a second confidence measurement value based on the second physiological parameter estimate and a second physiological data reference;

activating at least one of deactivated wavelength emissions when the confidence measurement value is greater than the threshold value.

13. The method of claim 11, wherein the physiological data reference comprises a normalized plethysmograph ratio region bounded by a high normalized plethysmograph ratio curve and a low normalized plethysmograph ratio curve.

14. The method of claim 13, wherein the high normalized plethysmograph ratio curve is a high oxygen saturation ($SpO_2$) curve and the low normalized plethysmograph ratio curve is a low oxygen saturation ($SpO_2$) curve.

15. The method of claim 11, wherein the physiological data reference comprises a reference parametric curve that is predetermined from clinically-derived data.

16. The method of claim 11, wherein the physiological data reference comprises a data cluster defining a region of normalized plethysmograph values.

17. The method of claim 11, wherein the second set of the plurality of wavelengths comprises two wavelengths.

18. The method of claim 17, wherein one of the two wavelengths is in the red range and the other of the two wavelengths is in the infrared range.

19. The method of claim 11, wherein the plurality of wavelengths comprises at least eight wavelengths.

20. The method of claim 11, wherein the physiological parameter measurement comprises a $SpO_2$, HbCO, HbMet, Hbt, factional oxygen saturation, bilirubin, or glucose measurement.

* * * * *